(12) United States Patent
Rowe

(10) Patent No.: US 11,585,743 B2
(45) Date of Patent: Feb. 21, 2023

(54) DETERMINING FORMATION POROSITY AND PERMEABILITY

(71) Applicant: Halliburton Energy Services, Inc., Houston, TX (US)

(72) Inventor: Mathew Dennis Rowe, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 301 days.

(21) Appl. No.: 17/006,396

(22) Filed: Aug. 28, 2020

(65) Prior Publication Data

US 2022/0065769 A1 Mar. 3, 2022

(51) Int. Cl.
| | |
|---|---|
| *G01N 15/08* | (2006.01) |
| *G01F 22/00* | (2006.01) |
| *G01N 33/28* | (2006.01) |
| *E21B 7/15* | (2006.01) |
| *H01J 37/32* | (2006.01) |
| *E21B 49/00* | (2006.01) |
| *G01N 33/24* | (2006.01) |

(52) U.S. Cl.
CPC ............ *G01N 15/088* (2013.01); *E21B 7/15* (2013.01); *E21B 49/003* (2013.01); *E21B 49/005* (2013.01); *G01F 22/00* (2013.01); *G01N 33/24* (2013.01); *G01N 33/2823* (2013.01); *H01J 37/32055* (2013.01)

(58) Field of Classification Search
CPC .. G01N 15/088; G01N 33/24; G01N 33/2823; E21B 7/15; E21B 49/003; E21B 49/005; G01F 22/00
See application file for complete search history.

(56) References Cited

U.S. PATENT DOCUMENTS

| | | | |
|---|---|---|---|
| 1,720,325 | A | 7/1929 | Hackstaff et al. |
| 2,328,555 | A | 9/1943 | Hoover, Jr. |
| 2,700,897 | A | 2/1955 | Arps |

(Continued)

FOREIGN PATENT DOCUMENTS

| | | |
|---|---|---|
| CN | 102678044 A | 9/2012 |
| CN | 202596572 U | 12/2012 |

(Continued)

OTHER PUBLICATIONS

"U.S. Appl. No. 17/006,051, Non-Final Office Action", dated May 2, 2022, 10 pages.

(Continued)

*Primary Examiner* — John Fitzgerald
(74) *Attorney, Agent, or Firm* — Delizio, Peacock, Lewin & Guerra

(57) ABSTRACT

Systems and methods are disclosed for using downhole plasma discharge effects to determine porosity and/or permeability of formation material. In some embodiments, a method includes determining a concentration of at least one chemical reaction product in a drilling fluid that has interacted with a plasma discharge proximate formation material. A relation between arc and spark of the plasma discharge is determined based, at least in part, on the at least one chemical reaction product, and at least one of porosity and permeability of the formation material is determined based, at least in part, on the relation between arc and spark.

20 Claims, 11 Drawing Sheets

(56) References Cited

U.S. PATENT DOCUMENTS

| | | |
|---|---|---|
| 4,536,713 A | 8/1985 | Davis et al. |
| 4,741,405 A | 5/1988 | Moeny et al. |
| 4,980,642 A | 12/1990 | Rodney |
| 5,005,406 A | 4/1991 | Jasinski et al. |
| 5,140,527 A | 8/1992 | Jones et al. |
| 5,163,029 A | 11/1992 | Bryant et al. |
| 5,896,938 A | 4/1999 | Moeny et al. |
| 6,026,099 A | 2/2000 | Young |
| 6,104,022 A | 8/2000 | Young et al. |
| 6,176,323 B1 | 1/2001 | Weirich et al. |
| 6,761,416 B2 | 7/2004 | Moeny |
| 7,124,030 B2 | 10/2006 | Ellis |
| 7,174,254 B2 | 2/2007 | Ellis |
| 7,337,660 B2 | 3/2008 | Ibrahim et al. |
| 7,384,009 B2 | 6/2008 | Moeny |
| 7,416,032 B2 | 8/2008 | Moeny et al. |
| 7,527,108 B2 | 5/2009 | Moeny |
| 7,529,626 B1 | 5/2009 | Ellis |
| 7,530,406 B2 | 5/2009 | Moeny et al. |
| 7,559,378 B2 | 7/2009 | Moeny |
| 7,571,644 B2 | 8/2009 | Ibrahim et al. |
| 7,959,094 B2 | 6/2011 | Moeny |
| 8,083,008 B2 | 12/2011 | Moeny |
| 8,172,006 B2 | 5/2012 | Moeny |
| 8,186,454 B2 | 5/2012 | Moeny |
| 8,567,522 B2 | 10/2013 | Moeny |
| 8,575,541 B1 | 11/2013 | Jamison et al. |
| 8,616,302 B2 | 12/2013 | Moeny |
| 8,789,772 B2 | 7/2014 | Moeny |
| 8,810,794 B2 | 8/2014 | Breviere et al. |
| 9,010,458 B2 | 4/2015 | Moeny |
| 9,016,359 B2 | 4/2015 | Moeny |
| 9,190,190 B1 | 11/2015 | Moeny |
| 9,328,594 B2 * | 5/2016 | Linetskiy ............ E21B 43/2401 |
| 9,335,438 B2 | 5/2016 | Jamison et al. |
| 9,700,893 B2 | 7/2017 | Moeny |
| 9,765,617 B2 | 9/2017 | Gosney et al. |
| 10,001,465 B2 | 6/2018 | Mitchell et al. |
| 10,113,364 B2 | 10/2018 | Moeny et al. |
| 10,371,691 B2 | 8/2019 | Strapoc et al. |
| 10,407,995 B2 | 9/2019 | Moeny |
| 10,641,073 B2 * | 5/2020 | Curlett .................... E21B 28/00 |
| 10,641,757 B2 | 5/2020 | Rowe |
| 11,319,788 B1 | 5/2022 | Shumway |
| 11,346,217 B2 | 5/2022 | Rowe |
| 11,459,883 B2 | 10/2022 | Rowe |
| 2005/0150688 A1 | 7/2005 | MacGregor et al. |
| 2006/0037516 A1 | 2/2006 | Moeny |
| 2007/0137893 A1 | 6/2007 | Moeny et al. |
| 2007/0152494 A1 | 7/2007 | Moeny |
| 2008/0147326 A1 | 6/2008 | Ellis |
| 2008/0277508 A1 | 11/2008 | Moeny |
| 2009/0126928 A1 | 5/2009 | Sumrall et al. |
| 2010/0089577 A1 | 4/2010 | Wideman et al. |
| 2010/0250142 A1 | 9/2010 | Zamora et al. |
| 2010/0326651 A1 | 12/2010 | Pietrobon |
| 2011/0000713 A1 | 1/2011 | Meeten et al. |
| 2011/0251795 A1 | 10/2011 | Difoggio |
| 2012/0298421 A1 | 11/2012 | Coates et al. |
| 2013/0032404 A1 | 2/2013 | Donderici et al. |
| 2014/0008968 A1 | 1/2014 | Moeny |
| 2014/0027178 A1 | 1/2014 | Jeffryes et al. |
| 2015/0068806 A1 | 3/2015 | Duran Toro et al. |
| 2015/0167440 A1 | 6/2015 | Kasevich et al. |
| 2015/0260035 A1 | 9/2015 | Rowe et al. |
| 2015/0268374 A1 | 9/2015 | Rapoport |
| 2015/0308235 A1 | 10/2015 | Moeny |
| 2015/0322326 A1 | 11/2015 | Van Slyke et al. |
| 2015/0354352 A1 | 12/2015 | Ezzat et al. |
| 2016/0010450 A1 | 1/2016 | Donderici et al. |
| 2016/0115786 A1 | 4/2016 | Breviere et al. |
| 2016/0153955 A1 | 6/2016 | Strapoc et al. |
| 2017/0058608 A1 | 3/2017 | Fraser et al. |
| 2017/0175505 A1 | 6/2017 | Curlett |
| 2017/0226851 A1 | 8/2017 | Hakim |
| 2018/0148981 A1 | 5/2018 | Moeny |
| 2019/0003298 A1 | 1/2019 | Stolyarov et al. |
| 2019/0226336 A1 | 7/2019 | Benson et al. |
| 2019/0368345 A1 | 12/2019 | Rowe et al. |
| 2019/0376386 A1 | 12/2019 | Wright et al. |
| 2020/0217143 A1 | 7/2020 | Liu et al. |
| 2020/0224498 A1 | 7/2020 | Liu et al. |
| 2021/0071489 A1 | 3/2021 | Jamison et al. |
| 2022/0065044 A1 | 3/2022 | Rowe |
| 2022/0065102 A1 | 3/2022 | Rowe |
| 2022/0065103 A1 | 3/2022 | Rowe |
| 2022/0065105 A1 | 3/2022 | Rowe |
| 2022/0065106 A1 | 3/2022 | Rowe |
| 2022/0065107 A1 | 3/2022 | Rowe |

FOREIGN PATENT DOCUMENTS

| | | |
|---|---|---|
| EP | 0700068 A1 | 3/1996 |
| EP | 1508794 A1 | 2/2005 |
| RU | 2477370 C1 | 3/2013 |
| WO | 9806234 A1 | 2/1998 |
| WO | 9937581 A2 | 7/1999 |
| WO | 2006023998 A2 | 3/2006 |
| WO | 2008097101 A1 | 8/2008 |
| WO | 2013110328 A1 | 8/2013 |
| WO | 2014100255 A1 | 6/2014 |
| WO | 2015124733 A2 | 8/2015 |
| WO | 2015154876 A1 | 10/2015 |
| WO | 2017030614 A1 | 2/2017 |
| WO | 2017146673 A1 | 8/2017 |
| WO | 2018071020 A1 | 4/2018 |
| WO | 2018136033 A1 | 7/2018 |
| WO | 2018186828 A1 | 10/2018 |
| WO | 2019245544 A1 | 12/2019 |
| WO | 2019245545 A1 | 12/2019 |

OTHER PUBLICATIONS

"U.S. Appl. No. 17/006,247 Office Action", dated Mar. 17, 2022, 6 pages.

"U.S. Appl. No. 17/006,254 Office Action", dated Mar. 3, 2022, 8 pages.

"Isotope Logging: Continuous isotopic ratio measurement service", [online] retrieved on Jun. 1, 2020 from https://www.slb.com/-/media/files/geoservices/product-sheet/isotope-logging-ps.ashx, 2015, 2 pages.

Behrends, et al., "Ultrasonic Relaxation and Fast Chemical Kinetics of Some Carbohydrate Aqueous Solutions", 1997 American Chemical Society, J. Am. Chem. Soc. vol. 119 No. 9, pp. 2182-2186.

Berner, et al., "Maturity Related Mixing Model for Methane, Ethane and Propane, based on Carbon Isotopes", Advances in Organic Geochemistry, vol. 13, No. 1-3, 1988, 6 pages.

Bruggeman, et al., "Non-Thermal Plasmas in and in Contact With Liquids", Journal of Physics D: Applied Physics 42, 2009, 28 pages.

Canonica, et al., "Quantitative Structure—Activity Relationships for Oxidation Reactions of Organic Chemicals in Water", Environmental Toxicology and Chemistry, vol. 22 No. 8, 2003, pp. 1743-1754.

Carrasquillo, et al., "Radical Reactivity in the Condensed Phase: Intermolecular Versus Intramolecular Reactions of Alkoxy Radicals", 2015 American Chemical Society, J. Phys. Chem. Lett. 6, pp. 2388-2392.

Chernyak, et al., "Plasma Catalysis of Chemical Reactions", Problems of Atomic Science and Technology, Series: Plasma Physics, 2014, pp. 124-129.

Cruse, et al., "Geochemistry of Low-Molecular Weight Hydrocarbons in Hydrothermal Fluids from Middle Valley, northern Juan de Fuca Ridge", Geochimica et Cosmochimica Acta, vol. 70, Issue 8, Apr. 15, 2006, 54 pages, https://doi.org/10.1016/j.gca.2006.01.015, 2006.

Donahue, et al., "New Rate Constants for Ten Oh Alkane Reactions From 300 to 400 K: an Assessment of Accuracy", 1998 American Chemical Society, J. Phys. Chem. vol. 102 No. 18, pp. 3121-3126.

Gierczak, et al., "Rate Coefficients for the Reactions of Hydroxyl Radicals With Methane and Deuterated Methanes", 1997 American Chemical Society, J. Phys. Chem. A vol. 101 No. 17, pp. 3126-3134.

(56) References Cited

OTHER PUBLICATIONS

Goddard, et al., "Novel Gas Isotope Interpretation Tools to Optimize Gas Shale Production", Report to Research Partnership to Secure Energy for America, 2013, 90 pages.
Hidenori, et al., "Streamer Discharges in Liquids and Their Applications", Institute of Electrical and Electronics Engineers Transactions on Dielectrics and Electrical Insulation vol. 7 No. 5, Oct. 2000, pp. 646-653.
Jiang, et al., "Review On Electrical Discharge Plasma Technology for Wastewater Remediation", Chemical Engineering Journal 236, 2014, pp. 348-368.
Kirkpatrick, et al., "Hydrogen, Oxygen, and Hydrogen Peroxide Formation in Aqueous Phase Pulsed Corona Electrical Discharge", 2005 American Chemical Society, Ind. Eng. Chem. Res. vol. 44 No. 12, pp. 4243-4248.
Kwok, et al., "Alkoxy Radial Isomerization in the Oh Radical-Initiated Reactions of C4-C8 N-Alkanes", 1996 American Chemical Society, J Phys. Chem. vol. 100 No 1, pp. 214-219.
Laroussi, "Low-Temperature Plasmas for Medicine?", Institute of Electrical and Electronics Engineers Transactions on Plasma Science vol. 37 No. 6, Jun. 2009, pp. 714-725.
Locke, et al., "Analysis and Review of Chemical Reactions and Transport Processes in Pulsed Electrical Discharge Plasma Formed Directly in Liquid Water", Plasma Chem Plasma Process, 2012, pp. 875-917.
Locke, et al., "Review of the Methods to Form Hydrogen Peroxide in Electrical Discharge Plasma With Liquid Water", Plasma Sources Science and Technology 20, 2011, pp. 1-15.
Malik, et al., "Water Purification by Electrical Discharges", Institute of Physics Publishing, Plasma Sources Science and Technology 10, 2001, pp. 82-91.
Medodovic, et al., "Primary Chemical Reactions in Pulsed Electrical Discharge Channels in Water", Journal of Physics D: Applied Physics 40, 2007, pp. 7734-7736.
Minakata, et al., "Development of a Group Contribution Method To Predict Aqueous Phase Hydroxl Radical (HO) Reaction Rate Constants", 2009 American Chemical Society, Environ. Sci. Technol. vol. 43 No. 16, pp. 6220-6227.
Minakata, et al., "Linear Free Energy Relationships Between Aqueous Phase Hydroxyl Radical Reaction Rate Constants and Free Energy of Activation", 2011 American Chemical Society, Environmental Science & Technology 45, pp. 3479-3486.
Nair, et al., "Mud Gas Isotope Logging using Mass Spectrometry", Society of Petroleum Engineers,2009 SPE Asia Pacific Oil and Gas Conference and Exhibition, Aug. 4-6, 2009, Jakarta, Indonesia, 13 pages.
Pironti, et al., "Determination of the 13C/12C Carbon Isotope Ratio in Carbonates and Bicarbonates by 13C NMR Spectroscopy", American Chemical Society, Analytical Chemistry 2017, 89, 21, 11413-11418, Sep. 13, 2017.
Pourzamani, et al., "Natural Organic Matter Degradation Using Combined Process of Ultrasonic and Hydrogen Peroxide Treatment", Geosciences Institute Yearbook UFRJ, vol. 38 No. 1, 2015, pp. 63-72.
Rao, et al., "Geochemical Assessment of Light Gaseous Hydrocarbons in Near-Surface soils of Kutch-Saurashtra: Implication for Hydrocarbons Prospects", Indian Academy of Sciences, J. Earth Syst. Sci. 122, No. 1, 2013, 9 pages.
Sahni, et al., "Quantification of Hydroxyl Radicals Produced in Aqueous Phase Pulsed Electrical Discharge Reactors", 2006 American Chemical Society, Ind. Eng. Chem. Res. vol. 45 No. 17, 2006, pp. 5819-5825.
Schoell, "Genetic Characterization of Natural Gases", The American Association of Petroleum Geologists Bulletin, V. 67, No. 12, 1983, 14 pages.
Shih, et al., "Chemical and Physical Characteristics of Pulsed Electrical Discharge Within Gas Bubbles in Aqueous Solutions", Plasma Chem Plasma Process, 2009, pp. 1-20.
Storey, et al., "Water Vapour, Sonoluminescence and Sonochemistry", Royal Society Publishing, Proc. R. Soc. Lend. A, 2000, pp. 1685-1709.
Sugiarto, et al., "Pulsed Plasma Processing of Organic Compounds in Aqueous Solution", Thin Solid Films 386, 2001, pp. 295-299.
Sugiarto, et al., "Transient Regime of Pulsed Breakdown in Low-Conductive Water Solutions", Institute of Physics Publishing, Journal of Physics D: Applied Physics 34, 2001, pp. 3400-3406.
Suhr, "Organic Syntheses Under Plasma Conditions", University of Tübingen, Germany, Department of Chemistry, pp. 395-414.
Suslick, et al., "Alkane Sonochemistry", 1983 American Chemical Society, J. Phys. Chem. vol. 87 No. 13, pp. 2299-2301.
Thagard, et al., "Plasma Chemistry in Pulsed Electrical Discharge in Liquid", Transaction of the Materials Research Society of Japan, 2009, pp. 257-262.
Zare, et al., "High-precision optical measurements of 13C/12C isotope ratios in organic compounds at natural abundance", Proceedings of the National Academy of Science of the United States of America, PNAS Jul. 7, 2009 106 (27) 10928-10932; https://doi.org/10.1073/pnas.0904230106.
PCT Application No. PCT/US2021/028780, International Search Report, dated Aug. 4, 2021, 3 pages.
PCT Application No. PCT/US2021/028780, Written Opinion, dated Aug. 4, 2021, 3 pages.
PCT Application No. PCT/US2021/031572, International Search Report, dated Aug. 23, 2021, 5 pages.
PCT Application No. PCT/US2021/031572, Written Opinion, dated Aug. 23, 2021, 5 pages.
PCT Application No. PCT/US2021/070776, International Search Report, dated Oct. 19, 2021, 5 pages.
PCT Application No. PCT/US2021/070776, Written Opinion, dated Oct. 19, 2021, 3 pages.
PCT Application No. PCT/US2021/070777, International Search Report, dated Oct. 18, 2021, 4 pages.
PCT Application No. PCT/US2021/070777, Written Opinion, dated Oct. 18, 2021, 6 pages.
PCT Application No. PCT/US2021/070815, International Search Report, dated Oct. 20, 2021, 3 pages.
PCT Application No. PCT/US2021/070815, Written Opinion, dated Oct. 20, 2021, 4 pages.
Bazargan, et al., "Wellbore Instability During Plasma Torch Drilling in Geothermal Reservoirs", 49th U.S. Rock Mechanics/Geomechanics Symposium, San Francisco, California, Jun. 28-Jul. 1, 2015, pp. 1-4.
Li, et al., "Influenceson High-Voltage Electro Pulse Boring in Granite", Energies, Sep. 17, 2018, vol. 11, No. 9, pp. 1-17, ISSN 2461.
U.S. Appl. No. 17/005,848 Office Action, dated Oct. 28, 2022, 26 pages.
U.S. Appl. No. 17/006,423 Non Final Office Action, dated Sep. 12, 2022, 16 pages.

* cited by examiner

DETERMINING FORMATION POROSITY AND PERMEABILITY

BACKGROUND

The disclosure generally relates to formation testing and in particular to using drilling fluid logging to determine formation properties.

During the drilling of a hydrocarbon-producing well, a drilling fluid or "mud" is continuously circulated from the surface down to the bottom of the wellbore being drilled and back to the surface again. The drilling fluid serves several functions including transporting wellbore cuttings up to the surface where they are separated from the drilling fluid. Another function of drilling fluid is cooling the drill bit and provide hydrostatic pressure on the walls of the drilled borehole to prevent wellbore collapse and the resulting influx of gas or liquid from the formations being drilled.

Analyzing the drilling fluid as it returns to the surface is an important initial appraisal of a potential hydrocarbon-bearing reservoir zone. Resultant data may be utilized to guide subsequent evaluation and testing within the well during drilling operations. Such test analysis is commonly referred to as "mud logging" analysis. Through mud logging, reservoir zones can be evaluated while they are being initially penetrated by measuring the liquid and gaseous components of formation fluids as well as material properties of formation solids (referred to as cuttings) present in the drilling fluid as it returns to the surface. The presence and concentration of hydrocarbon and non-hydrocarbon fluids and properties of formation solids in drilling fluids relative to the depth may be used to design stimulation operations and production operations, as well as in the initial formation quality assessment. Determining formation properties such as porosity and permeability typically requires bulk measurements of relatively large samples of downhole cuttings.

BRIEF DESCRIPTION OF THE DRAWINGS

Embodiments of the disclosure may be better understood by referencing the accompanying drawings.

DESCRIPTION

The description that follows includes example systems, methods, techniques, and program flows that embody aspects of the disclosure. However, it is understood that this disclosure may be practiced without these specific details. For instance, this disclosure refers to pulsed direct current (DC) plasma in illustrative examples. Aspects of this disclosure can be also applied to sustained or alternating current (AC) plasmas. Additionally, while analysis may be described in reference to being performed at the surface of the borehole, example embodiments can include at least a partial analysis downhole. For example, some or all of the analysis can be performed in a downhole tool of the drill string. In other instances, well-known instruction instances, protocols, structures, and techniques have not been shown in detail in order not to obfuscate the description.

Overview

Conventional wellbore drilling includes rotary drilling using a rotating drill bit having cutting elements to cut rock such as by fracturing or crushing. Pulse power drilling drills a wellbore using electric pulses that include short duration, periodic, high-voltage pulses that are discharged through rock within a surrounding formation. Such discharges generate high internal pressure to break or fracture the rock from the inside (breaking from tension).

Pulse power drilling typically generates a high energy fluid in the form of a plasma in the drilling fluid or rock downhole. Plasma, which is the fourth state of matter, may be a highly conductive, ionized gas containing free electrons and resultant positive ions from which the electrons were disassociated. In the high-temperature and high-pressure downhole environment, plasma is generated by injecting large amounts of energy into the subsurface formation. The injected energy is expended as a mechanical fracturing (e.g., tearing or crushing) force and a portion may also be absorbed by downhole fluids including formation fluid and drilling fluid.

In response to the injected energy, ionic bonds within the formation material are broken and formation fluid vaporized. The energy output from the pulse power drill bit may also induce chemical reactions between downhole chemical species. These chemical reactions can generate chemically complex molecules that may be identified and measured to facilitate determination of formation properties such as porosity and permeability. The concentration of chemical species and cuttings returned to the surface may be correlated to plasma generation parameters for formation evaluation generally and including determining porosity and permeability values that can be used to modify or update drilling operations.

Example Illustrations

Figure 1:
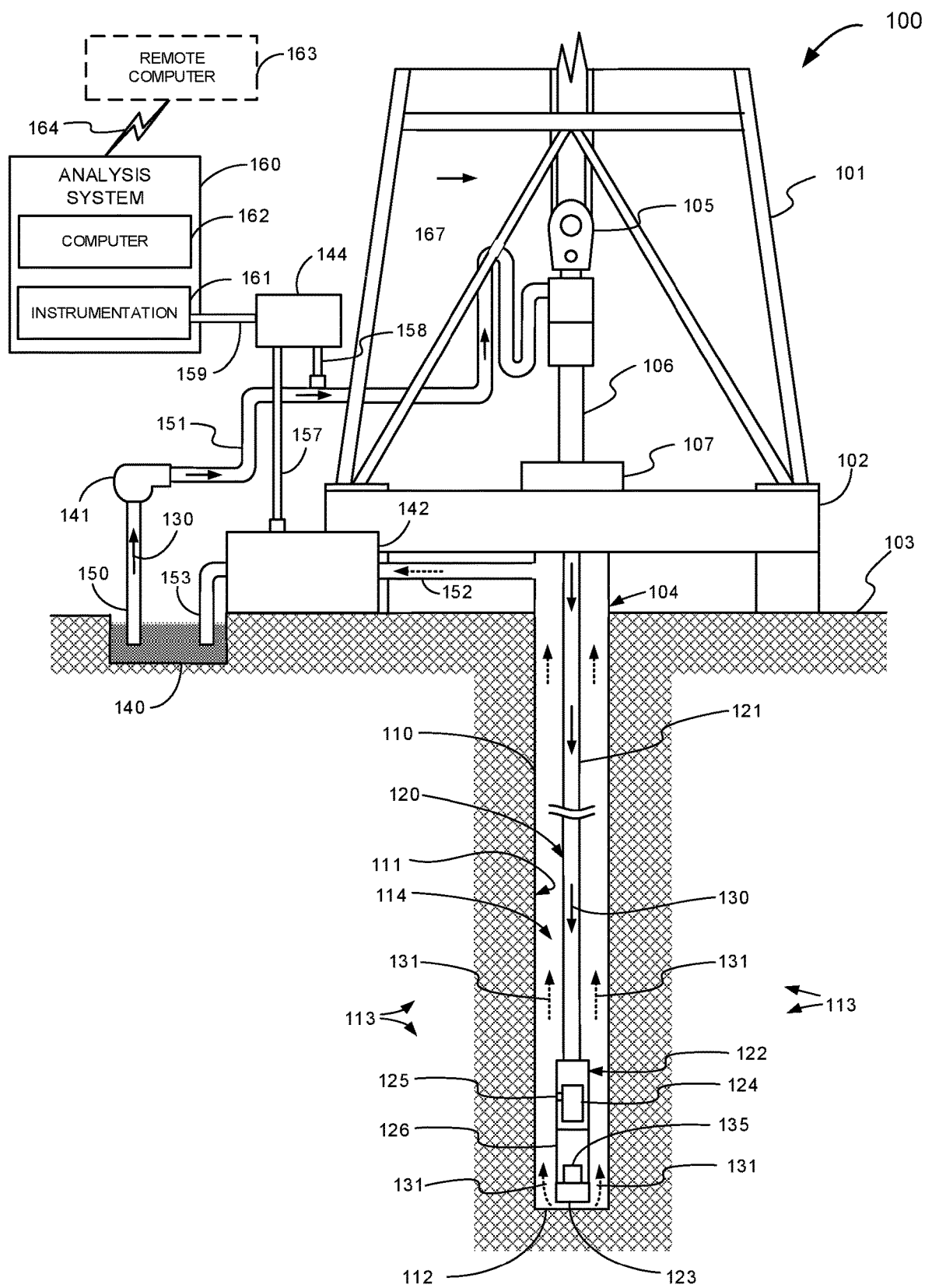
FIG. 1 depicts an example pulse power drilling system for mud logging, according to some embodiments.

FIG. 1 illustrates a schematic diagram of a pulse power drilling system (a system 100), according to one or more embodiments. System 100 includes a derrick 101 positioned on a platform 102 that is located above a surface 103 and covering a wellhead 104. Wellhead 104 includes drilling and/or production equipment positioned over a borehole 110 that extends from surface 103 into one or more layers of a subterranean formation 113. Borehole 110 includes borehole walls 111 that extend downwardly from surface 103 and form the space within the borehole that extends from surface 103 to a borehole bottom surface 112. Although shown as having substantially a vertical orientation in FIG. 1, embodiments of borehole 110 are not limited to vertically orientated boreholes, and may include at least some portion(s) of the borehole that extend at an angle relative to vertical, including in some embodiments portions of the borehole that may extend horizontally in a direction parallel to surface 103.

System 100 includes a drill string 120 extending downward into borehole 110. Drill string 120 may be supported at an upper portion by a hoist 105 suspended from derrick 101 that allows drill string 120 to be controllably positioned at different depths within borehole 110. Drill string 120 may be coupled to a hoist 105 through a kelly 106 and may extend through a rotary table 107 positioned adjacent to and/or extending though an opening in a platform 102. Rotary table 107 may be configured to maintain the position of drill string 120 relative to platform 102 as drill string 120 is extended through the opening in platform 102 and into borehole 110. Drill string 120 may comprise a plurality of sections of drill pipe 121 coupling a lower or distal end of drill string 120 to a bottom hole assembly (BHA) 122. BHA 122 includes a pulse power drilling (PPD) assembly 126 having electrodes of a drill bit 123 and a pulse-generating circuit 135.

A drilling fluid 130, also referred to as drilling mud, may be initially sourced from a fluid pit 140, which may be referred to as a "mud pit." Although depicted below surface 103, fluid pit 140 may be located on or above surface 103. A pump 141 may be used to suction drilling fluid 130 from fluid pit 140 through a conduit 150, and provide a pressurized flow or circulation of drilling fluid 130 through a conduit 151 to the upper portion of drill string 120, as illustratively represented by the solid line arrows within conduits 150 and 151. Drilling fluid 130 may then proceed through the sections of drill pipe 121 that make up portions of drill string 120, providing a fluid passageway for drilling fluid 130 to flow from the upper portion of drill string 120 to BHA 122.

The flow of drilling fluid 130 is directed through BHA 122 and expelled from one or more ports included in drill bit 123. Drilling fluid 131, as illustratively represented in FIG. 1 by dashed-line arrows, that has been expelled from ports on, or through, drill bit 123 helps to remove formation material, also referred to as cuttings, that have been broken up by the electrical energy generated by the electrodes of drill bit 123 in a direction away from the electrodes and away from a borehole bottom surface 112.

In addition to carrying away formation cuttings, the flow of a drilling fluid 131 may also have been exposed to or otherwise interacted with the electrical energy applied by the electrodes of drill bit 123 to borehole bottom surface 112 and/or to the fluids proximate the electrodes of drill bit 123. Drilling fluid 131 is illustrated as broken-line arrows to represent drilling fluid that may have one or more chemical properties and/or one or more physical properties that have been altered due to the interaction with the injected energy. The flow of drilling fluid 131 continues to flow back upward toward surface 103 through annulus 114 of borehole 110. Annulus 114 is formed by the space between borehole walls 111 and the outer surfaces of drill string 120. Drilling fluid 130 flowing into drill string 120 from fluid pit 140 may be referred to as inflow or influent, and drilling fluid 131 flowing from ports within drill bit 123 back to fluid pit 140 may be referred to as return flow or effluent. Together, influent drilling fluid 130 and effluent drilling fluid 131 form an open or closed loop drilling fluid circulation system.

When drilling fluid 131 reaches surface 103, the flow may be directed into conduit 152, which directs the flow of returning drilling fluid 131 to a reconditioning system 142. Reconditioning system 142 may comprise any number of devices, such as shakers, screens, and/or wash stations, which are configured to process drilling fluid 131, for example to remove and/or recover cuttings from drilling fluid 131 being processed. In one or more embodiments, reconditioning system 142 may include one or more of de-salters, de-sanders, and de-gassing apparatus. Reconditioning system 142 may process drilling fluid 131 to refine or alter other properties of drilling fluid 131, for example to remove dissolved or suspended gasses present in drilling fluid 131. Reconditioning system 142 may also be configured to add chemicals, such as high dielectric constant muds or clays, conductive nanoparticle suspensions, weighting agents, etc., to drilling fluid 131 to alter or reinforce various performance properties of drilling fluid 131 before return/recirculation into drill string 120. Upon completion of the processing through reconditioning system 142, drilling fluid 131 may be returned to fluid pit 140 through a conduit 153.

An extraction system 144 is fluidly coupled to the flow path of drilling fluid 131 via a conduit 157 running from reconditioning system 142 to extract an effluent sample of drilling fluid 131 that has exited borehole 110 via conduit 152. Extraction system 144 may also be coupled to conduit 151 via conduit 158 to extract an influent sample of drilling fluid 130 prior to its entering into drill string 120.

Extraction system 144 may include one or more gas extractors configured to extract gas samples from effluent drilling fluid 131 and/or influent drilling fluid 130. Extraction system 144 may including one or more sampling apparatus to sample or extract the liquid or gaseous portion of the fluid, or both. Extraction system 144 is configured to sample gas or liquids directly from reconditioning system 142 or from another point in the flow of drilling fluid 131 from borehole 110 or the flow of drilling fluid 130 into drill string 120.

In various embodiments, a portion of returning drilling fluid 131 is directed to a sample analysis system 160 from extraction system 144. Extraction system 144 directs drilling fluid (e.g., effluent drilling fluid 131) extracted or sampled from reconditioning system 142 or influent conduit 151 to analysis system 160 via a conduit 159. In one or more embodiments, extraction system 144 extracts or samples influent drilling fluid 130, e.g., from conduit 151 or from one or more other points in the influent side of the system, such as conduit 150 or directly from fluid pit 140.

Figure 9:
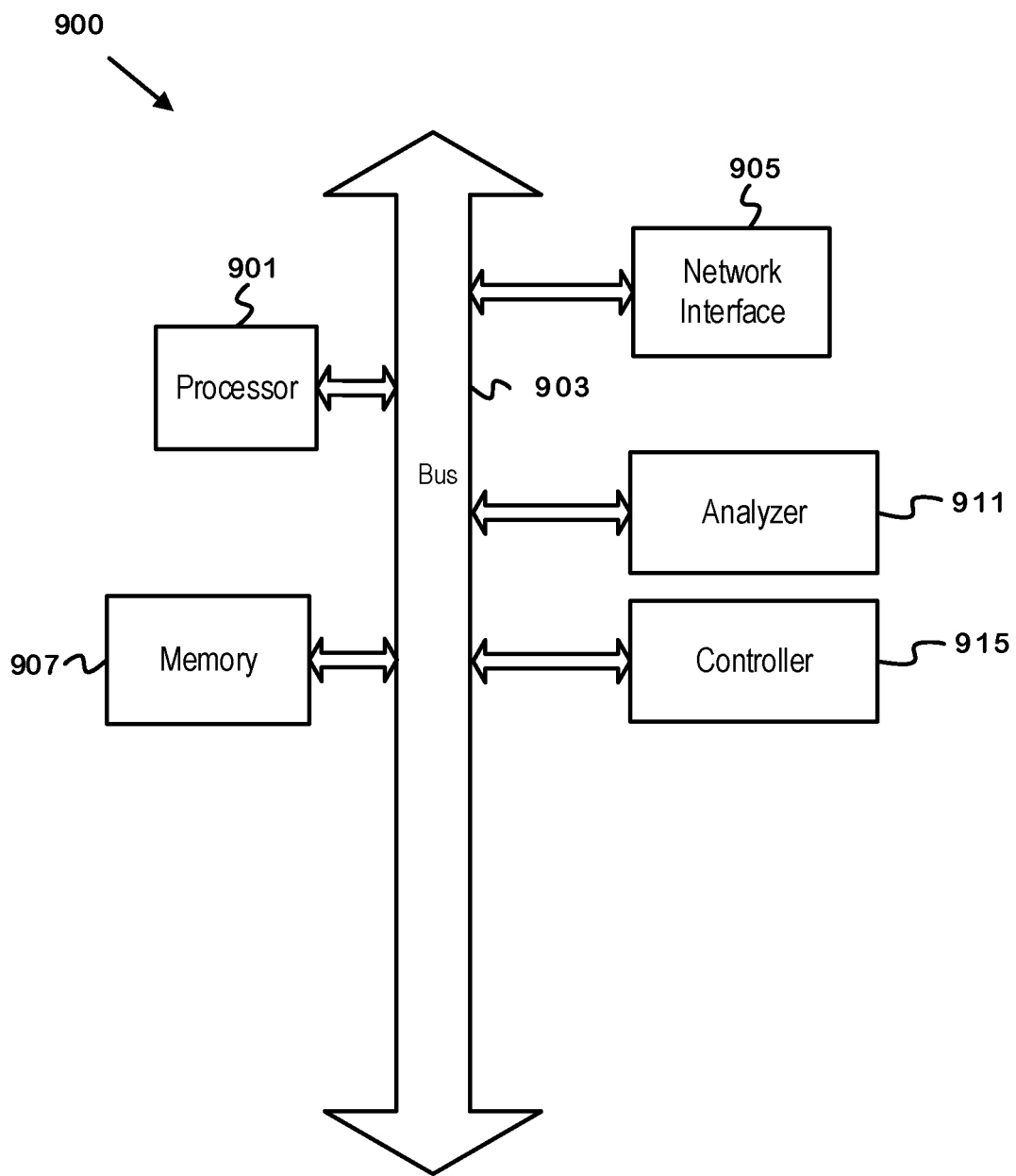
FIG. 9 depicts a computer system for implementing aspects of formation testing in accordance with some embodiments.

Analysis system 160 includes an instrumentation 161 and a computer 162. An example of computer 162 is depicted in FIG. 9, which is further described below. Instrumentation 161 may comprise one or more devices configured to measure and/or analyze one or more chemical and/or physical properties of the drilling fluid provided to analysis system 160. Illustrative and non-limiting examples of the devices that may be included as part of instrumentation 161 include one or more gas chromatograph (GC) (e.g., one or more of a gas chromatography—isotope ratio mass spectrometer (GC-IRMS), gas chromatography—infrared isotope ratio analyzer (GC-IR2), dual gas chromatograph with a flame ionization detector (FID), or the like) and one or more mass spectrometer (e.g., one or more of an isotope ratio mass spectrometer (IRMS), magnetic sector mass spectrometer, Time-of-Flight mass spectrometer (TOF-MS), triple quadrupole mass spectrometer (TQMS), tandem mass spectrometer (MS/MS), thermal ionization-mass spectrometer (TIMS), inductively coupled plasma—mass spectrometer (ICP-MS), Spark Source mass spectrometer (SSMS), or the like). Instrumentation 161 may further include one or more of a liquid chromatograph, a laser spectrometer, a multivariate optical computing device (e.g. one or more integrated optical element), a nuclear magnetic resonance (NMR) measurement device, a cavity ring-down spectrometer, an electromechanical gas detector, a catalytic gas detector, an infrared gas detector, a cutting analysis tool or system for further analysis of the gas, liquid, and/or solids. Instrumentation 161 may also include one or more temperature sensors for measuring the temperature of the effluent and/or influent samples and can include one or more pressure sensors to measure the pressure of the effluent and/or influent samples. These sensors or other sensors can also be distributed at different points along the fluid circulation path, such as in extraction system 144, pump 141, BHA 122, drill string 120, annulus 114, along any of conduits 150-159, and/or at another point in the fluid circulation path.

Instrumentation 161 may provide one or more measurements and other determined outputs to computer 162 that can be used as inputs for further analysis, learning, calculation, determination, display, or the like. The fluid samples received by, or continuous measurements obtained by, analysis system 160, e.g. as inputs to computer 162, may be correlated with time, depth, and/or other information related to the interaction of the fluid sample with electrical energy emanating from the electrodes of drill bit 123. For example, a sample of drilling fluid may be correlated to a specific time and/or a depth where a drilling fluid sample was when the fluid interacted with the electrical pulse energy generated by drill bit 123. In some embodiments, this correlation is based, at least in part, on the measured rates for flow of the drilling fluid down through drill string 120 and back up through annulus 114 over time to determine when the sample of drilling fluid being analyzed interacted with the electrical energy provided by the electrodes of drill bit 123.

Computer 162, in some embodiments, is integral with one or more of the devices including instrumentation 161, and/or may comprise separate computer device(s) that may be communicatively coupled to the devices included in instrumentation 161. In other examples, computer 162 may be computing devices, such as personal computers, laptop computers, smartphones, or other devices that allow a user, such as a field technician or an engineer, to enter, observe, and otherwise interact with various software applications providing data reports and control inputs for the measurements and analysis being performed on the drilling fluid by analysis system 160.

In various embodiments, although not shown, computer 162 may be communicatively linked with other devices, such as BHA 122, pump 141, extraction system 144, and/or reconditioning system 142. The communication provided between computer 162 and other device within system 100 may be configured to allow computer 162 to adjust operating parameters, such as but not limited to adjusting the flow rates of drilling fluid provided to drill string 120, controlling the positioning of drill string 120 with borehole 110, and controlling the operating parameters associated with the power level and/or energy consumption of drill bit 123. Communications from computer 162 may also be used to gather information provided by reconditioning system 142, and/or to provide feedback to reconditioning system 142 to control the processes being performed on the returning drilling fluid.

Analysis system 160 and extraction system 144 are configured to determine one or more of the drilling fluid composition, formation fluid composition, and isotope ratio from influent 130 and from effluent 131. For example, the extracted sample from influent 130 can be used as a baseline to evaluate the composition of effluent 131 to determine the contribution of the formation fluid and/or a downhole reaction at drill bit 123.

Analysis system 160 may determine various parameters related to formation 113, and/or various parameters related to the operation of PPD assembly 126, based on measurements and/or analysis performed to determine various chemical and/or physical properties present in the drilling fluid that has been exposed to or that has otherwise interacted/reacted with the electrical pulse energy from drill bit 123. Further, various operating parameters, such as electrical parameters, associated with the discharge of the electrical energy from the electrodes of drill bit 123, may be measured and analyzed to derive data and make determinations about various parameters associated with formation 113, parameters associated with properties of the drilling fluid, parameters associated with the operating parameters of BHA 122, and/or parameters associated with the operating parameters of PPD assembly 126.

System 100 may include a communication link 164 configured to provide communications between analysis system 160 and one or more onsite and/or offsite computer systems 163. Computer systems 163 may be configured to provide any of the data functions associated with and/or the analysis function described above that may be associated with the drilling fluid. Computer systems 163 may include data storage devices, such as magnetic, optical, or semiconductor devices, configured to store data generated by analysis system 160. Computer system 163 may include display devices, such as computer monitors, that allow users at remote locations to visualize and interact with the visual representations of the data provided by analysis system 160. In various examples, control inputs, as described above, may be provided via user input provided to computer systems 163 and communicated to analysis system 160 to control one or more of the operating parameters associated with system 100.

In some embodiments, BHA 122 includes a sampling tool 124 that may be located within the housing of BHA 122. Sampling tool 124 may be coupled to annulus 114 through port 125, wherein port 125 provides a fluid communication passageway between annulus 114 and sampling tool 124. Port 125 may be used to collect drilling fluid samples, such as samples of return drilling fluid 131. The drilling fluid samples may be measured and analyzed by internal tools within sampling tool 124 and/or provided to instrumentation 161 that performs measurements and/or further analysis of the drilling fluid. Measurements made, such as by one or more pressure or temperature sensors and/or a multivariate optical computing device, and/or data collected from the analysis of the samples may be communicated through a communication link, e.g., via wired (like a wireline or wired pipe) or wireless telemetry (like mud pulse, acoustic, or electromagnetic telemetry) to the surface, and optionally to analysis system 160. In the alternative or in parallel with the above, the drilling fluid samples may be contained within sampling tool 124 and subsequently transported back to the surface. Records for drilling fluid samples collected via port 125 may be data stamped with information indicating the time, depth, and/or other information associated with the collection of the respective samples.

Figure 2:
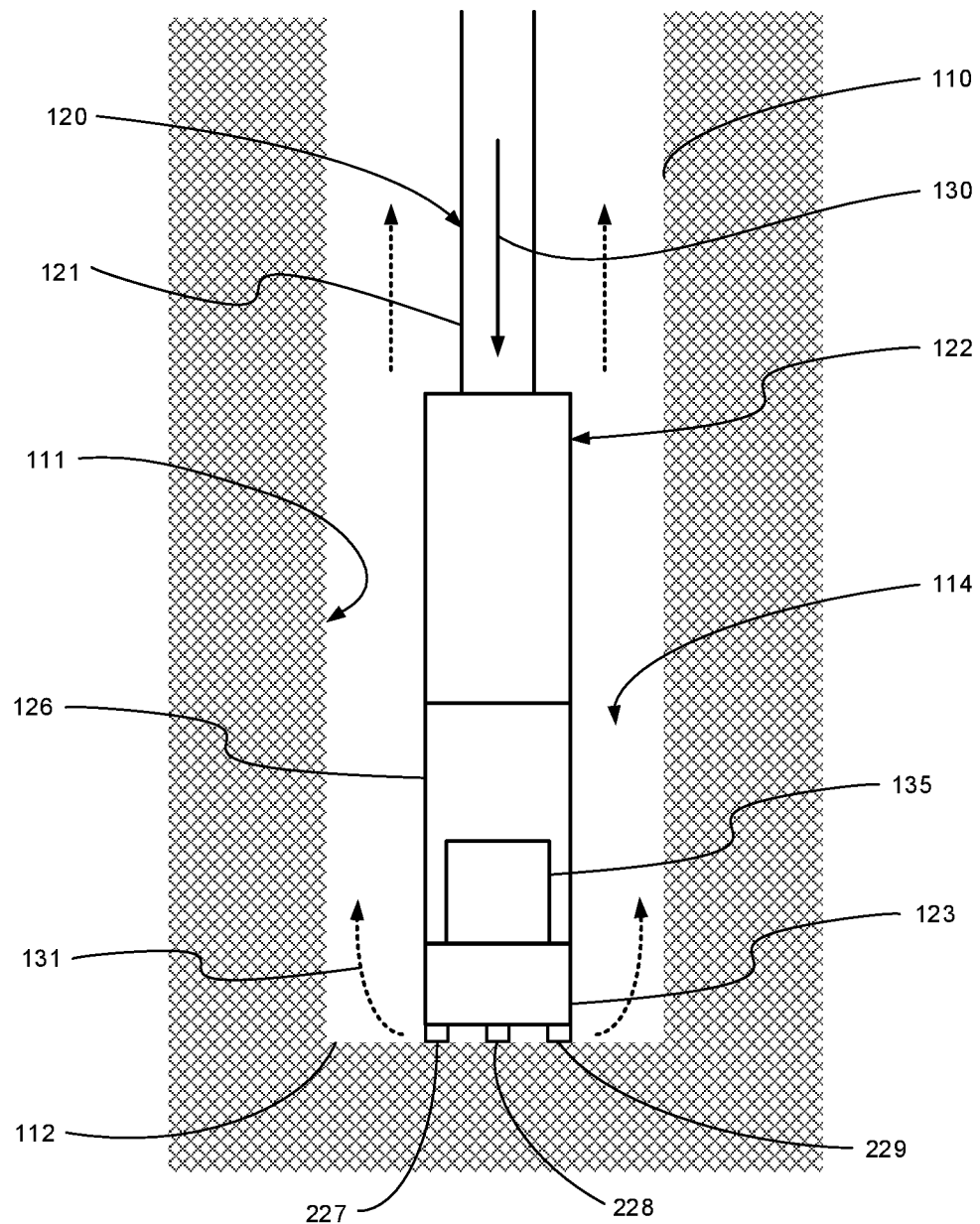
FIG. 2 illustrates a schematic diagram of an enlarged portion of the pulsed power drilling system shown in FIG. 1.

FIG. 2 illustrates a schematic diagram of an enlarged portion of system 100, according to some embodiments. As depicted in FIG. 2, drill bit 123 has one or more electrodes (three electrodes 227-229 are shown) disposed on a surface of drill bit 123 that faces borehole bottom surface 112. In one or more embodiment, the drill bit 123 may have at least one central electrode 228 and at least one outer electrode, e.g., a first outer electrode 227 and a second outer electrode 229. While three electrodes are depicted, two or more electrodes can be used. Further, the electrodes can be arranged differently on and around drill bit 123. For example, multiple outer electrodes may be spaced azimuthally around an outer circumference of drill bit 123. In yet another configuration, electrode 228 can include multiple central electrodes, for example azimuthally distributed around a central point and radially closer to the central point than at least one of the outer electrodes. Although not shown, in at least one embodiment, one or more ground rings may be disposed proximate to or touching the circumference of the bottom of drill bit 123, for example replacing, or disposed proximate to but not touching, the one or more outer electrodes. At least one of the electrodes can act as an anode and another as a cathode. For example, in one or more configurations and/or one or more operating modes, central electrode 228 may be configured and operate as an anode and at least one of the first and second outer electrodes 227, 229 may be configured and operate as a cathode. In one or more other configurations and/or one or more other operating modes, outer electrode 227 may be configured and operate as an anode and at least one of central electrodes 228 and outer electrode 229 may be configured and operate as a cathode.

PPD assembly 126 can be configured to supply power to drill bit 123 and ultimately to at least one of the one or more electrodes 227-229 via pulse-generating circuit 135. In some embodiments, power is supplied to PPD assembly 126 from the surface, via one or more wires or via wired pipe. In other embodiments, PPD assembly 126 is configured to generate electrical energy produced from a mechanical flow of drilling fluid provided to the bottom hole assembly through fluid passageways provided within drill pipes 121. For example, while passing through BHA 122, the flow of drilling fluid can be channeled through a turbine/alternator sub-assembly included in BHA 122 (not specifically shown in FIG. 1). The turbine/alternator sub-section can be configured to convert the energy from the flow of drilling fluid into a mechanical rotational energy, which is turn can be used to drive an alternator portion of the sub-assembly, and thereby generate electrical power. The generated electrical power may then be conditioned and controllably applied to drill bit 123.

The electrical energy generated by the PPD assembly 126 may be controllably applied to the drill bit 123 and thereby to at least one of the one or more electrodes 227-229 via pulse-generating circuit 135. Pulse-generating circuit 135 may be utilized to repeatedly apply a large electric potential, for example over 30 kV, over 75 kV, over 100 kV, or up to or exceeding 150 kV, across one or more of the electrodes 227-229. Each application of electric potential is referred to as a pulse. When the electric potential across electrodes of drill bit 123 becomes sufficiently large, a high current, high power electrical discharge or plasma arc forms through the material forming formation 113 and/or effluent drilling fluid 131 that is near electrodes 227-229. The plasma arc provides a temporary electrical short between the electrodes, and thus allows electric current to flow through the arc inside a portion of the material forming formation 113 and/or effluent drilling fluid 131 at borehole bottom surface 112. The plasma arc greatly increases the temperature and pressure of the portion of material forming formation 113 through which the arc flows and the surrounding formation and materials. The temperature and pressure are sufficiently high to vaporize any water or other fluids that might be proximate to or encompassed by the arc and may also vaporize part of the rock itself. The vaporization process creates a high-pressure gas and/or a plasma, which expands and, in turn, fractures the surrounding material forming formation 113.

The electrical energy, when applied for example to borehole bottom surface 112, acts to break up formation 113 in the vicinity of the at least one of the one or more electrodes 227-229, and thus advance the borehole 110 through the material forming formation 113. The exposure of the formation 113 and the drilling fluid to the electrical energy discharged from the drill bit 123 may, in additional to breaking up formation material, cause one or more downhole reaction that alters one or more chemical and/or physical properties of the formation material and/or drilling fluid that has been exposed to or has otherwise interacted with the electrical energy provided by drill bit 123.

Figure 3A:
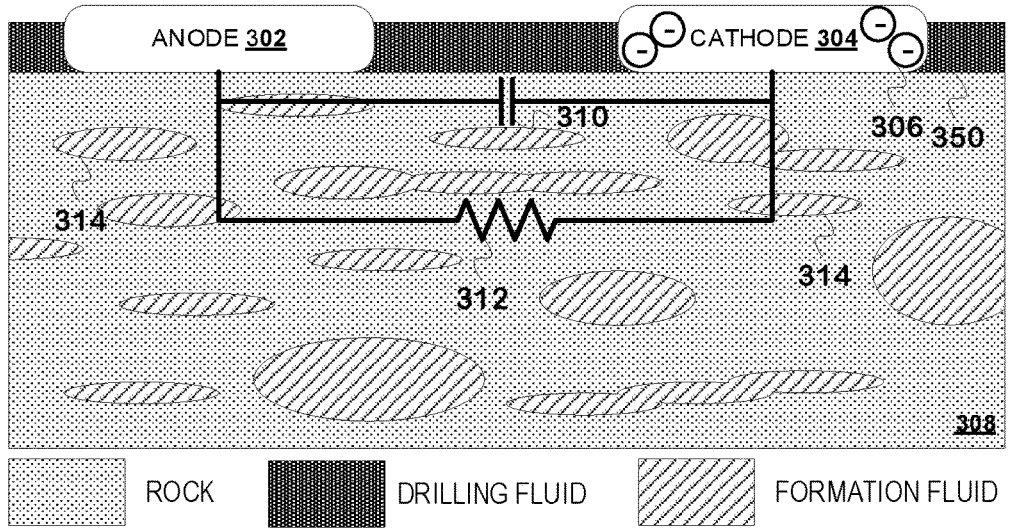
FIG. 3A depicts electrodes of a pulse power drill string at the bottom of a wellbore prior to emission of a pulse into the formation, according to some embodiments.
Figure 3B:
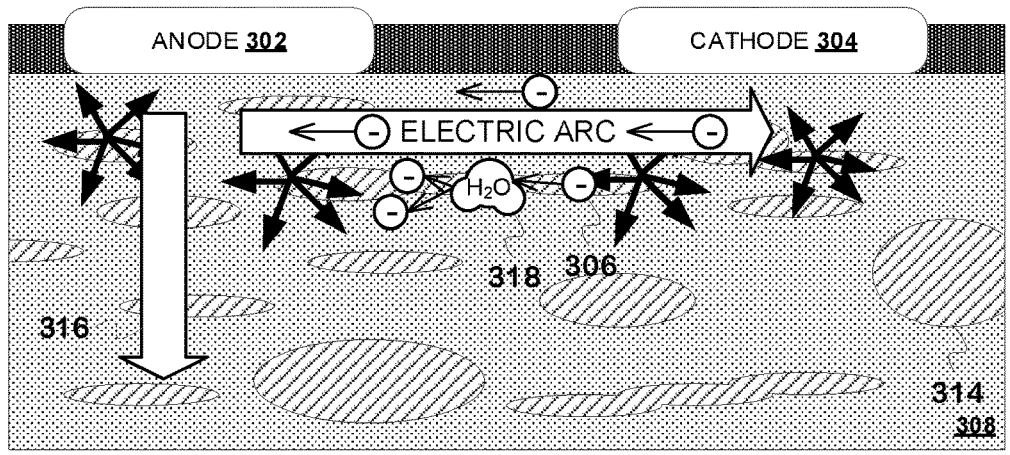
FIG. 3B illustrates the electrodes of a pulse power drill string during emission of a pulse into the formation, according to some embodiments.
Figure 3C:
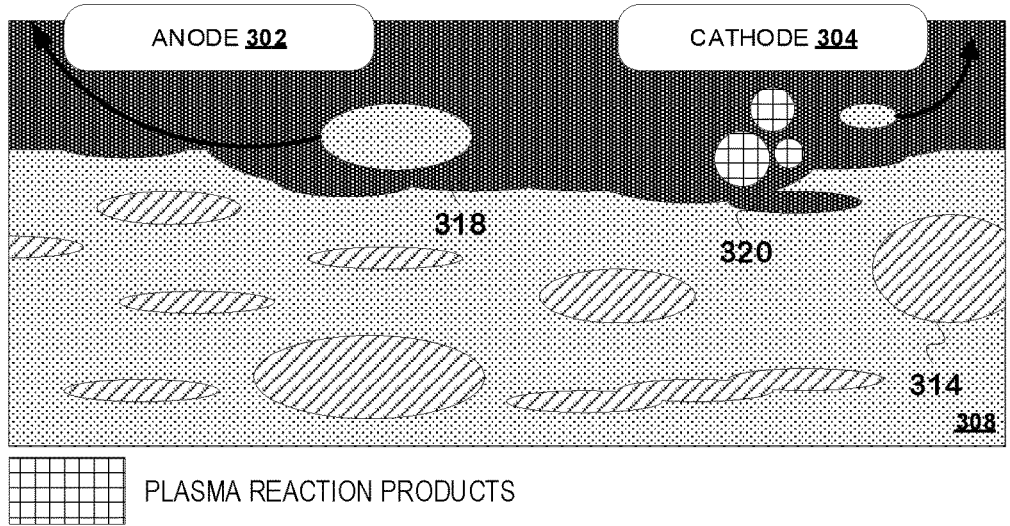
FIG. 3C depicts electrodes of a pulse power drill string at the bottom of a wellbore after emission of a pulse into the formation, according to some embodiments.

FIGS. 3A-3C depict electrodes of a pulse power drill string at the bottom of a wellbore at three different points in time relative to the emission of a pulse into the formation, according to one or more embodiments. FIG. 3A depicts electrodes of a pulse power drill string at the bottom of a wellbore prior to emission of a pulse into the formation, according to some embodiments. In this example, a drill bit includes electrodes depicted as an anode 302 and a cathode 304. Anode 302 and cathode 304 can be examples of the electrodes within drill bit 123 of drill string 120 of FIG. 1.

In pulse power drilling, anode 302 and cathode 304 (when not performing off-bottom analysis) may be positioned at a bottom surface 350 of the wellbore in contact with a formation 308. Formation 308 includes a number of pore spaces 314 having formation fluid. One or more of the electrodes can be charged by portions of the drill string as described above. This charging can induce charge carriers in the form of electrons and holes at the electrode formation interface with electrons 306 depicted.

The dielectric between anode 302 and cathode 304 may comprise of the formation rock or stone, the formation fluid in the pores of the rock strata, and/or the drilling fluid pumped downhole. Prior to generating a plasma, the dielectric may be approximated as a resistor 312 in parallel as depicted (or alternatively in series) with a capacitor 310, in which the dielectric strength may be a function of porosity, permeability, formation type, formation fluid composition, and drilling fluid composition.

FIG. 3B depicts the electrodes of a pulse power drill string of FIG. 3A during emission of a pulse into formation 308, according to some embodiments. As shown in FIG. 3B, a plasma discharge into formation 308 can result in vaporization of the fluid in pore spaces 314, which causes expansion of the liquid in the pores as it is converted to a high-pressure vapor or gas, resulting in tension-induced rock fracturing. Formations without pore spaces, or with small, impermeable pore space, are also susceptible to pulse power drilling. In such dry formations, the plasma discharge occurs through the rock itself, which then incurs dielectric material breakdown, creating fissures and fault lines along the current path.

Vaporization of fluid is a faster pulse power drilling method, but both mechanisms may be active in the same formation material (e.g., rock and/or liquid components) simultaneously.

At the pressure and temperature of a wellbore, the ideal gas law may not provide an accurate approximation of a volume of a gas. A gas volume for hydrocarbons is modeled using the Wilson model, or another thermodynamically complex model or approximation. The volume of gas (such as $H_2$, $CO_2$, etc.) generated downhole—but not the volume of vapor generated (such as steam)—can be calculated from the volume of gas evolved at the surface. The volume of gas detected at the surface can be converted to a molar amount via the ideal gas law (see Equation 1 below).

$$PV=nRT \quad (1)$$

Where P is pressure, V is volume, n is the number of moles of the gas, R is the ideal or universal gas law constant and T is temperature in Kelvin. At high temperatures and pressures downhole, the ideal gas law approximation can be inaccurate and gas volume is calculated using Wilson's equation for a multi-component fluid (see Equation 2 below) or a similar equation.

$$\ln[\gamma_k] = 1 - \ln\left[\sum_{j=1}^{n}(x_j A_{kj})\right] - \sum_{i=1}^{n}\left[\frac{x_i A_{ik}}{\sum_{j=1}^{n}(x_i A_{ij})}\right] \quad (2)$$

Wilson's model determines the liquid phase activity coefficient γ for component k as a function of the molar fraction $x_n$ of each of n components, where Aij, Aji are the Wilson coefficients for the binary pair of components i and j. The liquid phase activity coefficient γ is related to the partial pressure of each compound in the fluid via Raoult's law (Equation 3) or a similar approximation.

$$p_k = x_k \gamma_k p_k^\sigma \quad (3)$$

In Raoult's law, $p_k^\sigma$ is the saturation pressure or vapor pressure of the undiluted $k^{th}$ component.

Current flows from anode 302 to cathode 304, which corresponds to a flow of electrons 306 from cathode 304 to anode 302. Electrons 306 are injected from cathode 304 into the dielectric under the influence of the electric field generated between anode 302 and cathode 304. The electric field can be approximated for a parallel plate capacitor as given by Equation 4:

$$E = \frac{\Delta V}{d} \quad (4)$$

where E is the electric field (in Volts (V) per meter or another unit) for a parallel plate capacitor approximation for electrodes separated by a distance d and at a voltage difference of ΔV. The electric field between anode 302 and cathode 304 is not uniform if the formation is not microscopically uniform, which is true for any formation strata with fluid filled pores. The average electric field can be approximated as shown in Equation 5:

$$\bar{E} \sim \frac{\Delta V}{d} \quad (5)$$

where $\bar{E}$ is the average electric field in the dielectric between the electrodes, ΔV is the voltage drop from anode to cathode (or between the electrodes, generally) and d is the separation distance between the electrodes.

Electrons 306 accelerate in the electric field in the dielectric until they collide with other charged or uncharged particles. The collision of charged particles in a plasma may generate an avalanche multiplication current, as described by Townsend (and further explained in reference to FIGS. 5A-5B). Similarly charged particles repel each other, but neutral and opposite polarity particles experience collisions at appreciable rates. Electron 306 collides with water molecule 318 resulting in the generation of an additional electron. This collision is governed by the hydroxide ion chemical formation relation represented by Equation 6:

$$e^- + H_2O \leftrightarrow \frac{1}{2}H_2 + HO^- + 2e^- \quad (6)$$

where $e^-$ represents electrons and $HO^-$ represents hydroxide ions. Another reaction pathway generates hydroxyl radicals but no additional electrons as shown in Equation 7:

$$e^- + H_2O \leftrightarrow \frac{1}{2}H_2 + HO\cdot + e^- \quad (7)$$

where HO. represents a neutral hydroxyl radical, and where free radicals or radicals are electrically neutral molecules with at least one unpaired electron and can be very reactive. In this way, the plasma generates high energy particle collisions that produce chemical reactions downhole.

For each plasma-generating pulse, some or all of the electric current travels between the cathode and anode as a plasma arc. A portion of all of the current may instead travel from one or both of the electrodes into the formation without reaching the other electrode in a phenomenon sometimes referred to as plasma sparking. The portion of the plasma power that generates a plasma spark 316 or sparking does not result in appreciable current transfer between the anode and cathode. Plasma sparks typically have higher temperatures than plasma arcs, as will be discussed in more detail below with reference to FIGS. 5A-5B. The differences in temperature and related properties affects the types of products generated and their reaction rates for plasma arcs versus plasma sparks. Plasma sparks contribute to vaporization and rock breakdown, but may form unevenly form at or from an electrode instead of dissipating power equally between both anode and cathode. While disadvantageous for continuous direction drilling, plasma sparks may be useful for modifying drilling direction.

FIG. 3C depicts electrodes 302 and 304 of a pulse power drill string at the bottom surface of a wellbore after emission of a pulse into the formation, according to some embodiments. The vaporization of the formation fluid generates expansive gases. As the plasma is quenched, the gasses are dissolved into the high-temperature and high-pressure drilling fluid. The formation solids (rocks or particulates), having been broken into smaller pieces by the plasma, are carried away as cuttings by the drilling fluid. The destruction of the solid formation matrix frees fluid 320 formerly trapped in pore spaces within the rock. However, fluid 320 from the regions where plasma was generated has been at least partially transformed into formation fluid containing plasma reaction products. The formation fluid containing plasma reaction products travels to the surface dissolved or otherwise combined with the drilling fluid to be analyzed and categorized.

Example Operations

Example operations are now described. The following description of example operations include Subsections A-C.

A. Example Pulse Power Mud Logging Operations

Figure 4A:
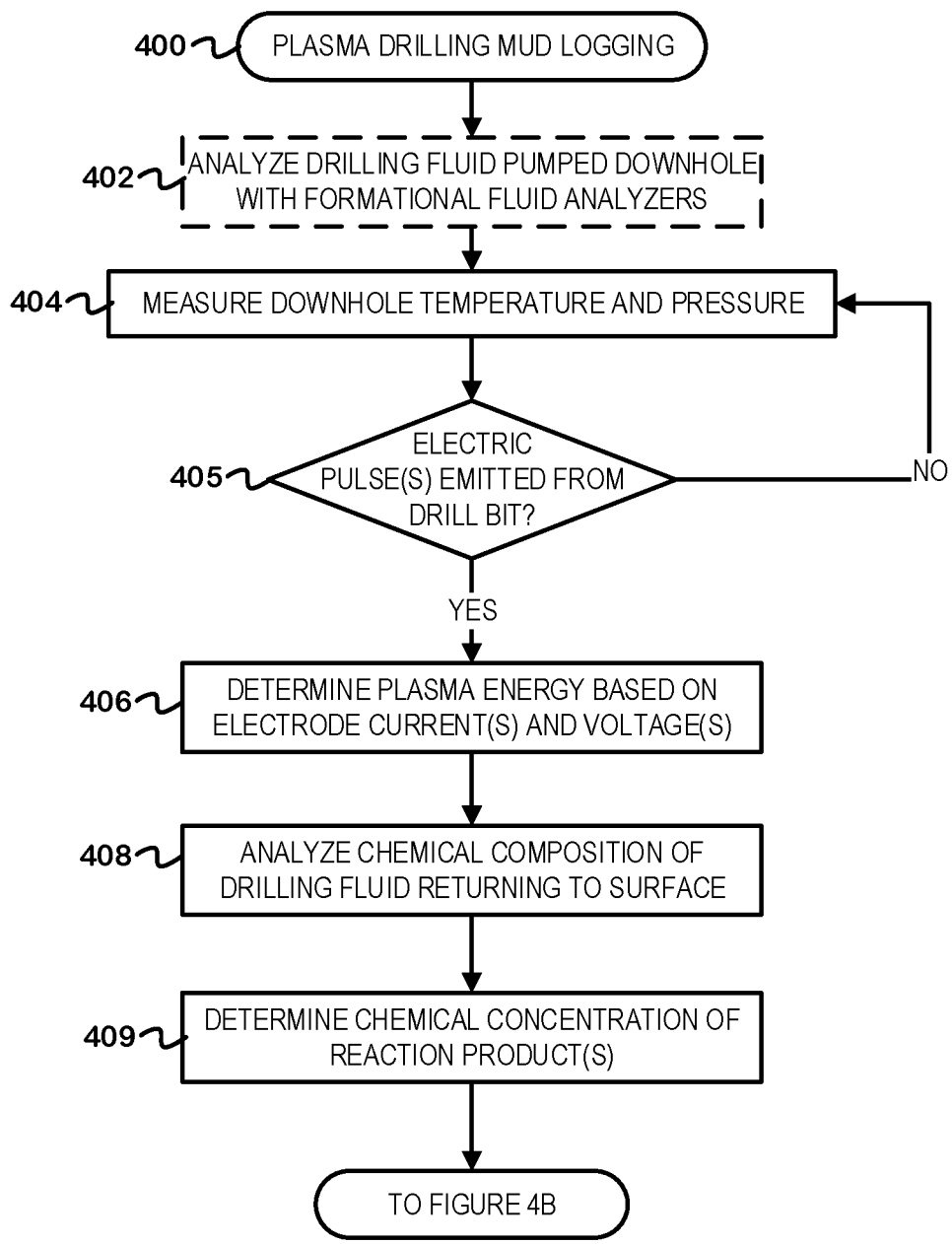
FIGS. 4A-4B illustrates a flowchart of example operations for pulse power mud logging, according to some embodiments.
Figure 4B:
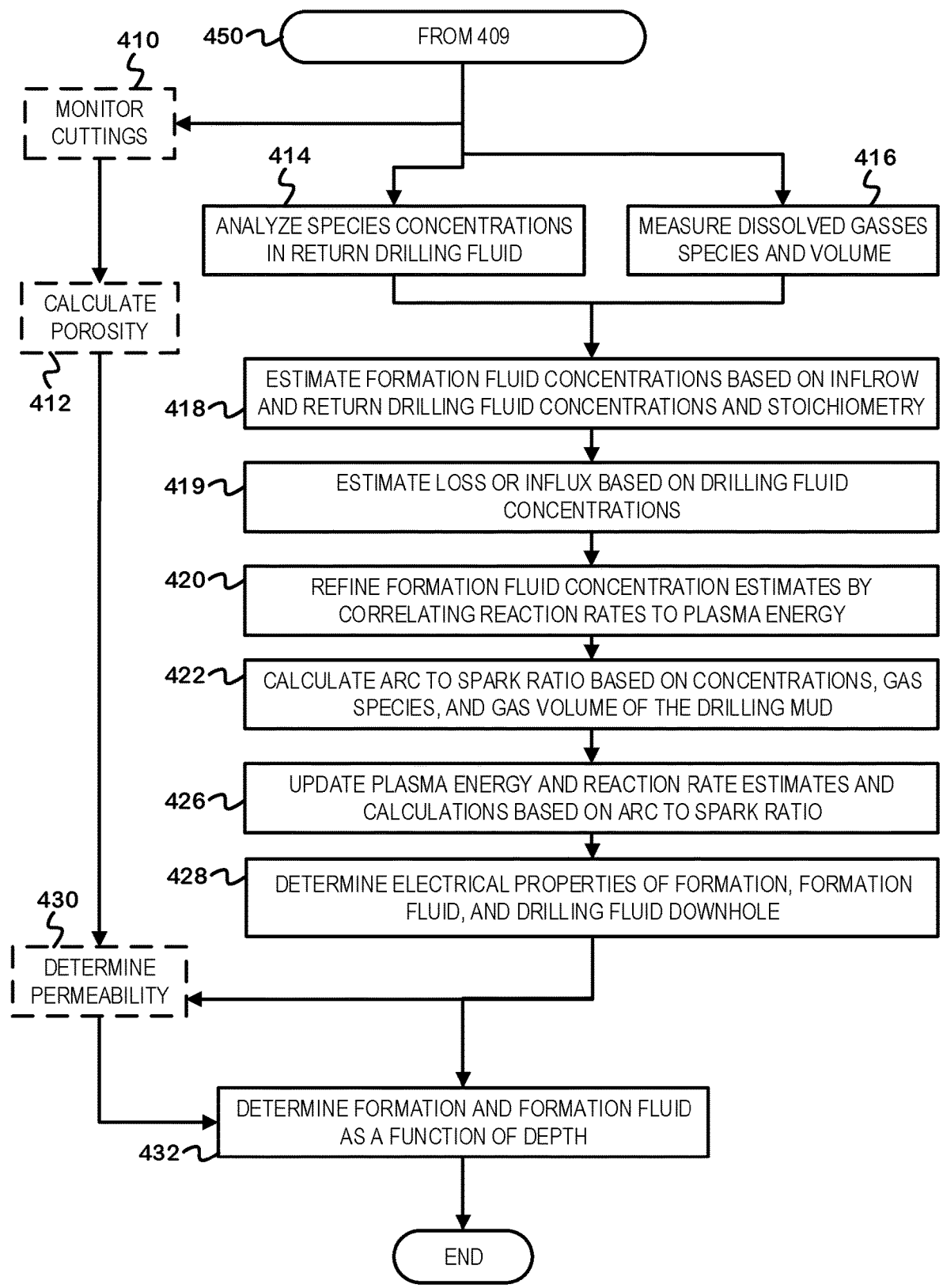

FIGS. 4A-4B depict a flowchart of example operations for pulse power mud logging, according to one or more embodiments. A flowchart 400 of FIG. 4A and a flowchart 450 of FIG. 4B includes operations described as being performed by the pulse power drilling and mud logging system devices and components such as depicted and described with reference to FIGS. 1, 2, and 3A-3C. Block 402 in FIG. 4A and blocks 410, 412, and 430 in FIG. 4B are depicted with broken lines to represent examples of operations that may be optionally performed. This depiction of the blocks of flowchart 400 and flowchart 450 should not be interpreted as requiring operations in the blocks depicted with solid lines, as one or more other operations in the solid blocks can be optional also.

FIGS. 4A-4B depict operations and functions related to plasma parameters, mud logging, and drilling optimization for an example pulse power drilling system. Pulse power mud logging includes several methods for determining formation fluid composition and generating mud logging records based on both downhole measurements and on fluid measurements and characterization. The relationship between the chemical composition of drilling fluid returned to the surface (including cuttings and solids, dissolved gasses, and liquid hydrocarbons) and the formation fluids entering the wellbore downhole is affected by the plasma generated by the pulse power drilling. By iteratively or sequentially solving a number of groups of equations and balances, the total degrees of freedom of the system can be reduced so that the problem is solvable—that is the formation fluid concentration can be determined or back calculated. The determination steps are shown here in a particular order, which is illustrative only, and it should be noted that each balance, set of equations, or determination can be applied in any order, including stepwise or iteratively.

At block 402, fluid analyzers are used to analyze drilling fluid to be pumped downhole. For example, with reference to FIG. 1, instrumentation 161 is configured perform this analysis as the drilling fluid enters the wellbore to be pumped downhole. The concentration of hydrocarbon species in the drilling fluid can measured using analyzers and detectors similar to those used to analyze the chemical composition of the drilling fluid returned to the surface in block 608. Optionally, the same analyzers may be configured and used to determine the composition of the drilling fluid returned to the surface and the drilling fluid entering the wellbore. Because the drilling fluid circulates through the wellbore, downhole chemical reactions cause drift in the drilling fluid's chemical composition. Measuring the drilling fluid's chemical composition as the fluid enters the wellbore enables the mud logging system to account for the initial concentration of hydrocarbons and water and determine the change in concentration for each iteration through the wellbore precisely as shown in Equation 8:

$$\Delta P = [P]_{product} = [P]_{exiting\ wellbore} - [P]_{entering\ wellbore} \tag{8}$$

where P is an example product molecule or species, [P] is a concentration of the example product and can be normalized for flow rate, rate (as of time), or volumetrically, and the concentration of P can change as a function of time of as a function of the total volume of drilling fluid. ΔP represents the total change in product in the drilling fluid due to one cycle through the wellbore and corresponding exposure to plasma.

In some embodiments, if the drilling fluid is not analyzed as it enters the wellbore, the drilling fluid composition is assumed from the chemical composition of the drilling fluid as it reaches the surface, which is determined at blocks 408 and 409, minus the concentration of gasses, which are removed from the drilling fluid before it enters the mud pit or another storage unit (as further described below in reference to block 416).

At block 404, downhole temperature and optionally downhole pressure are measured. For example, with reference to FIG. 1, computer 162 may be configured to perform this operation. The temperature of the drilling fluid affects the reaction rate constants and plasma parameters, such as breakdown voltage, dielectric constant, etc. The mud logging system is configured to correlate the downhole temperature to drilling fluid analyzed at the surface by adjusting for drilling fluid pumping speed that may be translated to volumetric flow rate and drilling speed.

At block 405, a determination is made of whether an electric pulse is emitted from the drill bit. As described above, the electrodes in the drill bit periodically emit an electric pulse to drill the borehole. For example, with reference to FIG. 1, computer 162 can determine when the electric pulse is emitted. If there is no electric pulse emitted, operations of flowchart 400 remain at block 404. Optionally, flow can continue to block 408 in the absence of a detected pulse and perform mud logging calculations based on possible plasma reaction products in drilling fluid that may result from previous reactions. The drilling fluid circulation time causes a temporal mismatch between when the pulse is detected and when the products are detected and analyzed at block 408. Otherwise, operations of flowchart 400 continue at block 406.

At block 406, the plasma energy is determined based on electrode current(s) and voltage(s). For example, with reference to FIG. 1, computer 162 can make this determination. The plasma energy can be determined based on anode and cathode current and voltage of the drill bit. Plasma power calculations can assume that power added to the system is approximately equal to the plasma power, or can account for power lost to the formation, heat of vaporization, etc.

In a closed-loop system where electrons are neither created nor destroyed, the current flowing through the system can be determined based on current measured at the anode (the anode current) and at the cathode (the cathode current) as given by Kirchhoff's current law. Kirchhoff's current law does not apply in a plasma, as the acceleration of electrons in the electric field of the plasma can cause Townsend avalanche multiplication, as will be discussed later. Electrons and positive ions can be created in the plasma. However, the electrons and positive ions can recombine when the plasma generation ends to form neutral molecules which are the reaction products. Once initiated, the plasma itself can be considered a conductor of infinite conductivity or zero resistance.

When the anode and cathode currents are equal and the plasma is quenched, no current flows into the formation or away to ground. If the anode and cathode currents are unequal, the difference can represent current lost to the formation or current created by the electrons and ions generated by the plasma. Current lost to the formation can be approximated as current lost to ground where the formation functions as a grounding electron sink. The relationship between anode, cathode, and formation current is then given by Equation 9 below:

$$I_{anode}=I_{cathode}+I_{formation}+I_{plasma} \quad (9)$$

Where $I_{anode}$ represents the current flowing out of the anode, $I_{cathode}$ represents the current flowing into the cathode, and $I_{plasma}$ represents any additional current generated by the plasma. $I_{formation}$ represents any current lost to the formation or otherwise away from the anode or cathode, or another electrode. For pulse power drilling in a wellbore, the formation current is approximately the ground current as shown in Equation 10, below:

$$I_{formation} \approx I_{ground} \quad (10)$$

Where $I_{ground}$ is the current lost to or gain from ground, which is approximately the formation or earth acting as an electron sink. $I_{formation}$ and $I_{ground}$ may or may not be measurable.

Plasma can form in the combination of drilling fluid, rock or formation, and formation fluid when the applied voltage is above the dielectric breakdown voltage of that combination, for the downhole temperature and pressure. At voltages above breakdown, electrons separate from molecules, generating positive ions. The electrons have much smaller mass than the positive ions and accelerate in the electric field towards the anode. In a low-pressure plasma, the mean free path of the electrons can be long, and the electrons may experience significant acceleration. Very fast electrons can generate additional electrons through the Townsend avalanche multiplication when they collide with positive ions or neutral molecules on their way to the anode. In a high-pressure plasma where free electrons can be drawn from ground, such as found when drilling in a formation, the mean free path of the electron can be so short that avalanche electron multiplication is negligible. In either case, the increase in current generated by the plasma is encompassed by the term $I_{plasma}$.

The value of the Townsend current, I, is given by Equations 11-12, below:

$$I = I_0 e^{\alpha_n d} \quad (11)$$

$$I = I_0 \frac{(\alpha_n - \alpha_p) \text{Exp}[(\alpha_n - \alpha_p)d]}{\alpha_n - \alpha_p \text{Exp}[(\alpha_n - \alpha_p)d]} \cong I_0 \frac{\text{Exp}[\alpha_n d]}{1 - \alpha_p / \alpha_n \text{Exp}[\alpha_n d]} \quad (12)$$

$I_0$ represents current generated at the cathode surface (which can be approximated as $I_0 = I_{cathode}$), $\alpha_n$ is the first Townsend ionization coefficient, $\alpha_p$ is the secondary ionization Townsend coefficient, and d is the distance between the anode and cathode of a parallel plate capacitive discharge. $\alpha_n$ represents the number of particle pairs generated by a negatively charged particle (anion or electron) per unit length, where such a negative particle is moving from cathode to anode. $\alpha_p$ represents the number of charged particle pairs generated per unit length by a cation, during its collisions while moving from anode to cathode. Equation 11 considers only electrons traveling at speeds sufficient to cause ionization collisions (i.e. a non-thermal plasma), while Equation 12 also considers positive ion (i.e. cation) traveling fast enough to impart ionization energy to neutral particles (i.e. a thermal plasma).

For a downhole plasma where d is known, the plasma current can be determined or estimated based on an exponential fit to the anode and cathode currents. The exponential portion of the increase in current during the lifetime of the plasma results from the avalanche multiplication in the plasma. Current lost to the formation or ground should exhibit only minimal capacitive or inductive charging (i.e. current that depend exponentially on time) and is predominantly resistive in nature and therefore distinguishable from the plasma current.

A plasma arc may be a plasma generated between the cathode and anode corresponding to a significant transfer of current balanced between anode and cathode. A plasma spark may be a non-directional or isotropic plasma without a directional current transfer. Plasma arcs are generated between the cathode and anode, and through a dielectric that can include any combination of formation fluid, formation, and drilling fluid. Plasma arcs can be detectable from their effect on the cathode and anode currents. Plasma sparks, where electrons are not accelerated appreciably between the cathode and anode, can be detectable via their drawn down of voltage (or power) from the anode and cathode. Plasma arc and plasma sparks can have fundamentally different plasma temperatures and geometries, which can lead to different high-energy transition states and chemical reactions, which will be discussed in more detail below in reference to FIGS. 5A-5B. For pulse power generation, the determination of a ratio between a plasma arc and plasma sparking can be estimated via electrical measurements and further or iteratively refined based on concentration of chemical products and determination of reaction rates from surface stoichiometric analysis.

The power added to the system can be determined by the current flowing through and the voltage drop over the system. If the cathode and the formation are at 0 volts (V) or ground, then the total power added to the system is given by the anode current multiplied by the anode voltage, as given by Equation 13:

$$P=I_{anode}V_{anode} \quad (13)$$

where P represents power in this instance (in units of Watts or equivalent), $I_{anode}$ is the current flow at the anode electrode, and $V_{anode}$ is the electric potential (or voltage) of the anode.

If the cathode is not also a ground source or if information about the current and voltage at the cathode is known, the power input into the system, P, is given by the approximation of Equation 15:

$$P=I_{anode}V_{anode}-I_{cathode}V_{cathode} \quad (15)$$

where $I_{cathode}$ is the current flow at the cathode electrode and $V_{cathode}$ is the cathode electrical potential in volts.

The plasma power, i.e., the power consumed to generate the plasma, can be assumed to account for the power input into the system. The plasma power approximation can be iteratively updated as a function of time. For a system where only the current at one electrode or the total power added to the system is known, the plasma power can be correlated to reaction rates, activation energies, and product concentrations instead of directly calculated. Pulse power discharges within similar formation material, under similar temperature/pressure conditions and determined to have similar power can be assumed to have similar properties, including spark vs. arc ratio, reaction rates, etc.

The power balance represents an instantaneous energy balance. The total energy balance of the system also provides information about the plasma power. For a plasma pulse of known duration, energy balance equations can be substituted for power balance equations. In this case, the total input energy to form the reaction products relates to the power or energy of the plasma. If reaction products and product concentrations of the chemical reactions are known, a total chemical energy balance can be determined based on the enthalpy of formation of the product species and the temperature and pressure at which the reactions occur.

The power or energy of an individual plasma pulse, or of multiple pulses over a specified interval, or the average power or energy of multiple pulses, may be correlated to the reaction products of such a reaction that reach the surface at a time delayed from the reaction. Traditional mud logging correlates drilling fluid chemical constituents to the depth at which they entered the borehole. Pulse plasma mud logging additionally correlates drilling fluid chemical constituents to a specific reaction time, current, and voltage in order to back calculate formation fluid properties. The lag between pulse power reaction and drilling fluid arrival at the surface is determined based on drilling rate, circulation rate, and drill depth.

A DC plasma current varies over time, even during the plasma pulse itself. Before the plasma is generated, the current is low and the resistivity of the dielectric between the anode and cathode (which can be modeled as the drilling fluid resistivity, formation rock resistivity, and formation fluid resistivity in parallel) is high. The voltage between the anode and cathode builds as the cathode is charged until the voltage applied over the dielectric is greater than the dielectric's breakdown voltage and a plasma is generated.

Plasma resistivity is relatively low and can be modeled as a zero resistivity conductor between the anode and cathode. If there are available free electrons in the system, an approximation applicable when electrons can be drawn from ground or stripped from water molecules in the drilling fluid, the current generated by the plasma can be estimated by the Townsend discharge equations (Equations 11-12, above) or determined via Kirchhoff's law from the other known currents.

A plasma is overall electrically neutral—the electrons generated by the avalanche cascade reactions are compensated by free electrons absorbed from ground or generated by ionization. The number of positive ions (cations) and electrons (where the contribution of anions can be approximated as $n_a \approx 0$) are approximately equal. The degree or fraction of ionization, f, for a plasma is given by Equation 16:

$$f_i = \frac{n_e}{(n_e + n_0)} \quad (16)$$

where $n_e$ is the number of electrons, $n_0$ is the number of neutral atoms or molecules, and $f_i$ is the ionization fraction.

Each particle in the plasma has a kinetic energy. Because there are so many electrons, ion, and atoms or molecules, the kinetic energy is often expressed as an energy distribution or particle temperature. The plasma temperature, T, of electrons for a Maxwell-Boltzmann distribution is given in Equation 17:

$$T_e = \frac{2}{3}\frac{\langle E \rangle}{k_B} \quad (17)$$

where $T_e$ is the electron temperature, $\langle E \rangle$ is the average plasma energy, and kB is the Boltzmann constant. The Maxwell-Boltzmann probability distribution describes a distribution of particle kinetic energy or speeds at thermodynamic equilibrium and is commonly used in statistical mechanics to approximate particle velocities and interactions as a function of temperature. Electron temperature is a fundamental measure of the energy of the electrons in a plasma and is used to calculate other plasma properties, such as collision rate, mean free path, etc, and is often given in units of Kelvin (K) or electron Volts (eV).

Plasmas are classified as either thermal, where anions, cations, and electrons have similar kinetic energy (i.e. are in thermal equilibrium) and non-thermal, where electrons alone have kinetic energy proportional to the plasma energy. The first plasma of the plasma pulses generated is generally a non-thermal plasma where the electrons of the plasma have a higher kinetic energy than the ions and molecules of the plasma. Thermal plasmas are generated from non-thermal plasmas as energy added to the plasma in the form of current and voltage increases the kinetic energy of the charged particles until they reach the same kinetic energy as the electrons. Thermal plasma are more common in alternating current (AC) and long lifetime plasmas, but can occur in DC plasmas and pulsed plasmas where the dielectric is sufficiently heated before the plasma is initiated (either by environmental heating or by previous plasma produced through the same dielectric). For a thermal plasma approximation shown in Equation 18:

$$T_a = T_c \approx T_h = T_e \quad (18)$$

particle temperatures include anion temperature $T_a$ and cation temperature $T_c$. Both anions and cations are more massive than electrons and having KE approximately equal to a heavy particle KE, corresponding to $T_h$. Energy is added to the motion of the charged particles by the electric field based on magnitude of the charge not polarity.

Reaction rate constants, also referred to as reaction coefficients, for reaction products generated in a plasma or at the quenching of the plasma depend on both the temperature of the plasma—electron temperature and heavy particle temperature—and upon the extent of ionization. By determining the reaction rates based on chemical concentrations in the drilling fluid, the plasma temperatures can be monitored.

The average plasma energy $\langle E \rangle$ is related to both the energy applied to the plasma and to the electron temperature. The plasma power corresponds to the electrical potential difference across the plasma (e.g., volts) and the current (e.g., amperes) through the electric field. Power and energy are related as shown in Equations 19 and 20:

$$\text{Power} = \frac{\text{Energy}}{\text{Time}} = \frac{\langle E \rangle}{\Delta t} \quad (19)$$

$$\text{Power} = \frac{\partial}{\partial t}\text{Energy} = \frac{\partial}{\partial t}\langle E \rangle \quad (20)$$

where power may also be represented as P, energy as E, average energy as $\langle E \rangle$, and where t is time.

Reaction rates are a function of plasma temperature, which corresponds to plasma energy. Therefore, plasma temperature can be calculated or correlated to measured reaction rates. Plasma power can be approximated from the power added to the system, and from the approximate plasma power and the plasma duration and an average plasma energy can be calculated. By comparing these two measures of plasma energy, the energy system can be checked for energy loss (i.e., energy lost to the formation can be detected). Either method can be used to approximate the other.

At block 408, the chemical composition of the drilling fluid returning to the surface is analyzed. For example, with reference to FIG. 1, instrumentation 161 is configured to perform the analysis. The drilling fluid can include both chemical reaction products and formation fluid acquired downhole, as well as solids in the form of formation cuttings. The drilling fluid can be separated by phase, where cuttings and other solids such as miscellaneous surface debris are removed. To illustrate, a shaker and/or screen can receive the drilling fluid from downhole and separate the cuttings and other solids from the drilling fluid. For example, with reference to FIG. 1, the fluid recondition system 142 can perform this separation. Instrumentation 161 analyzes the solids at block 410 of FIG. 4B. The drilling fluid logging system separates dissolved gasses via low-temperature or low-pressure separation from the hydrocarbon liquids. The gasses are then analyzed at block 416 of FIG. 4B, before being disposed of or safely stored. A portion of the filtered drilling fluid can be diverted to allow instrumentation 161 to analyze this fluid for chemical composition at block 414 of FIG. 4B.

At block 409, the chemical concentration of the reaction product is determined. For example, with reference to FIG. 1, the computer 162 can make this determination based on the instrumentation 161 or the analysis system 160. The chemical concentration can be measured in weight per volume (such as grams per liter g/L), moles per volume (such as moles per liter mol/L), weight percent (such as nanograms per milliliter ng/mL), parts per million (ppm), mole percent or mole fraction (such as mol compound/mol total or mol %), etc. The chemical concentration can be measured for a specific amount of drilling fluid, or as a function of drilling rate or time.

At block 410, the cuttings can be analyzed to determine the volume of rock returned to the surface. For example, with reference to FIG. 1, instrumentation 161 can analyze the cuttings. Methods of cutting measurement include optical scanning and image processing to determine particle size distribution, weighing of cuttings, and calculating volume based on a measured density (where the density is measured using a core sample or periodically for each formation layer), or via a large bore Coriolis density meter.

At block 412, porosity is determined based on the measurement of cuttings that occurred at block 410. For example, with reference to FIG. 1, computer 162 can make this determination in part by reconstructing the total volume of rock removed from the formation. Computer 162 is further configured to compare that volume as a function of time to the drilling rate to determine the ratio of rock to pore space in the formation layer being drilled. The pore fraction $\phi$ is given by Equation 21:

$$\phi = \frac{V_v}{V_T} \tag{21}$$

where the pore fraction $\phi$ is a dimensionless number representing the portion of the rock volume occupied by pores and where $V_T$ is the total volume and $V_V$ is the void volume. Void volume can be correlated to pore shape, pore size, and pore throat size (where pore throat size is a determining factor in permeability).

Porosity and permeability of the formation information can be determined in traditional mud logging from information about changes in the volume of drilling fluid and from measurements on the size and volume of cuttings. The plasma reaction downhole in pulse power drilling converts a portion of the drilling fluid and formation fluid to gas. Once the mass balance of the reaction is determined, the original volume of downhole fluid is determined. Based on the volume calculation, the drilling fluid volume is further subtracted and the remaining volume is a measure of formation fluid volume as a function of drilling depth. By accounting for formation fluid volume per unit of depth drilled, the percentage of formation rock that constitutes formation fluid space is calculated as a measure of porosity. The volume of rock fragments measured at the surface and the calculate pore volume equal the total volume drilled, as a function of time. Each method can therefore function as a check on the value of the other.

At block 430, permeability is determined based on porosity and electrical characteristics of plasma discharge. For example, with reference to FIG. 1, computer 162 is configured make this determination.

At block 414, the chemical composition of the fluid is determined. The chemical composition of the fluid can include various hydrocarbons and water. Computer 162 may determine which chemicals are present and their concentration levels. Computer 162 may make this determination using instrumentation 161 that can include application of gas chromatography, liquid chromatography, mass spectrometry, absorption or emission spectrometry, nuclear magnetic resonance spectrometry (NMR), or the like.

At block 416, the molar concentrations of gasses produced by the plasma reaction is determined. The molar amount of gas produced can be determined based on the volume of gas detected at the surface, using the ideal gas law where each mole of gas corresponds to 22.4 L at standard temperature and pressure (STP).

At block 418, the formation fluid concentrations are estimated based on the concentrations of species in the drilling fluid and estimated stoichiometry of a chemical reaction. The chemical reaction may be more specifically a dehydrogenation reaction, in which hydrogen gas is produced from hydrocarbons as they form more saturated bonds (i.e. more double bonds). Computer 162 can determine the change in drilling fluid species concentration by subtracting the concentrations of species found in the drilling fluid pumped downhole (from block 402, 408, or 409 depending on drilling configuration). Based on the change in concentration that corresponds to the influx of formation fluid and chemical reactions generated by the plasma in the fluid at the drill bit, computer 162 may solve the system of equations corresponding to the stoichiometric relationships and to the reaction rate equations between the products and the potential reactants. For known or solvable stoichiometry, reactant concentrations can be calculated directly. For most systems, the stoichiometric equations generate a set of solvable equations with more degrees of freedom than encompassed by product concentration alone. For these systems, estimated reaction rate constants and reaction kinetics can be applied in order to determine reactant concentrations.

Drilling fluid for traditional mechanical drilling requires properties that promote mechanical drilling and support pore pressure: i.e. density, viscosity, etc. Drilling fluid for pulse power drilling is also an electrical transportation medium, which determines, at least in part, electrical properties, such as dielectric constant, breakdown voltage, resistivity, etc. Both electrical and structural properties depend on chemical concentration of the constituent molecules are particulates of the drilling fluid which is monitored in traditional mud drilling. Therefore, mud logging for pulse power drilling may also include calculating the stoichiometry and reaction rate of the chemical reactions occurring downhole.

The rate at which a chemical reaction takes place, i.e. the rate at which reactants turn into products, is given by a generalized reaction rate, which depends on a reaction rate constant k(T) and on the concentration of reactants (e.g., units of moles per unit volume). The reaction rate constant k may be a function of temperature, pressure, and activation energy. The reaction rate for a generalized m+n$^{th}$ order reaction for a rate limiting step involve molecules of species A and B is shown in Equation 22:

$$r=k(T)[A]^m[B]^n \qquad (22)$$

where r is the reaction rate, k(T) is the reaction rate constant, A and B are reactant molecules and the rate limiting step involves m molecules of reactant A interacting with n molecules of reactant B, such as for a reaction mechanism described by a rate limiting intermediate step shown in Equation 23 below:

$$m \cdot A + n \cdot B \rightarrow q \cdot P \qquad (23)$$

Where m molecules of A and n molecules of B react to form q molecules of an example product molecule P.

The order of the reaction (zeroth order, first order, etc.) depends upon the reaction mechanisms and the rate limiting step in the reaction and how many and which species of molecules participate in the rarest or slowest collision. The rate limiting step is usually the slowest step of the elementary or intermediate steps that make up the reaction mechanism. For many chemical reactions, the reaction mechanism or the set of intermediate steps that occur when reactants become products has a single step or portion that is observably slower than all other steps. This step functions as a bottleneck or limit on the total reaction speed, and is therefore known as the rate limiting step. For a reaction with multiple intermediate steps, the rate limiting step can depend on a catalyst molecule that is not a reactant or a product. For direct current (DC) plasmas with lifetimes in the microsecond (µs) to second range, many hydrocarbon formation reactions depend on intermediate steps involving hydroxyl free radicals, carbonyl free radicals or other free radicals with very short lifetimes, where free radical formation is therefore the rate limiting step. Hydroxyl free radical formation and concentration is dependent on water concentration, not hydrocarbon concentration, and upon plasma energy and properties including plasma temperature and geometry. This gives rise to many zeroth and first order reaction rates for generation of alkenes, alkynes, aromatics, and other unsaturated hydrocarbons from alkanes. A zeroth order reaction rate, as shown in Equation 24, does not depend on the concentration of the reactants and have a rate constant with units of mol/s or equivalent. The zeroth order reaction rate may be calculated or otherwise represented as, $$r=k(T)[A]^0=k(T) \qquad (24)$$

where r is the reaction rate, k(T) is the reaction rate constant for a reaction with the rate limiting step that is independent of reactant concentration and where [A] is a reactant concentration. A first order reaction rate depends in the first order (i.e. [A]$^1$) on a reactant and has a rate constant with units s$^{-1}$ or equivalent, as is shown in Equation 25:

$$r=k(T)[A] \qquad (25)$$

where r and k(T) are the reaction rate and reaction rate constant, respectively, and A is a reactant.

The reaction rate constant k(T) depends on temperature and may be approximated using the Arrhenius equation, as shown in Equation 26 below:

$$k(T)=Ae^{-E_a/RT} \qquad (26)$$

The Arrhenius equation relates the reaction rate constant k to the activation energy $E_a$, the absolute temperature T in kelvin, the universal gas constant R, and a pre-exponential factor A representing the fraction of molecular collisions resulting in the chemical reaction out of all molecular collisions of the species of the rate limiting step. Alternatively, the Boltzman constant $k_B$ can be used in place of R if the activation energy $E_a$ is also in units of $k_B T$. An exponential fitting factor β can also be used to correct modeled data to experimental data, as is shown for Equation 27:

$$k(T) = A\mathrm{Exp}\left[-\left(\frac{E_a}{RT}\right)^\beta\right] \qquad (27)$$

where β is a dimensionless fitting factor used to relate reaction rate constants to observable reaction rates, as a function of temperature.

Formation fluid can be approximated to a first order as containing alkanes, naphthenes (generic name for the cycloalkanes family), and water. Alkanes, having the general chemical formula $C_nH_{2n+2}$, contain single carbon to carbon bonds (σ bonds) between n sp$^3$ hybridized carbon atoms. Alkanes are saturated hydrocarbons which contain no carbon-carbon double bonds (π bonds) but are rather full hydrogenated—that is the carbon backbone or carbon chain is bonded to the maximum number of hydrogen atoms possible. Napthenes, which are cyclic alkanes where the carbon chain loops back on itself, have the general chemical formula $C_nH_{2(n+1-r)}$ where n is the number of carbons in the cycloalkane and r is the number of rings in the naphthene molecule. Formation fluid can also contain water, such as salt water, when emanating from water rich rock formations or strata. The generalized chemical equation for the plasma reaction is approximated by Equation 28, below.

$$A_n \cdot C_nH_{2n+2} + B_{n,r} \cdot C_nH_{2(2+1-r)} + D \cdot H_2O \rightarrow E_n \cdot C_nH_{2n+2} + \\ F_{n,r} \cdot C_nH_{2(n+1-r)} + G_n \cdot C_nH_{2n} + I_n \cdot C_nH_{2n-2} + J \cdot CO_2 + \\ K \cdot O_2 + L \cdot H_2 \qquad (28)$$

The stoichiometric coefficients for each of the hydrocarbon species (i.e. $A_n$, $B_{n,r}$, $E_n$, $F_{n,r}$, $G_n$ and $I_n$) depend both on the number of carbon atoms for the type of hydrocarbon (i.e., n) and the isomer (or atomic arrangement) of those carbon atoms, but can be approximated as independent of isomeric configuration in order to simplify measurements. Table 1, below, contains names and formulas alkanes, alkenes, and alkynes as a function of the number of carbons they contain. As the molecules become larger (i.e., as n increases) the number of isomer molecules for each chemical formula increase, where isomers are various physical arrangements and chemical bonds possible for the same atoms. For n>2, polyunsaturated hydrocarbons also occur (i.e. hydrocarbons with two or more double bonds). Unsaturated hydrocarbons such as alkanes, are carbon molecules that contain only hydrogen and carbon and have the maximum number of hydrogen constituents possible for the given amount of carbon atoms. The ability to detect or differentiate hydrocarbons, including isomers, from one another depends on the specificity of instrumentation.

TABLE 1

Common Hydrocarbons

| N | Formula | Alkane | Isomers | Formula | Alkene | Isomers | Formula | Alkyne | Isomer |
|---|---|---|---|---|---|---|---|---|---|
| 1 | $CH_4$ | Methane | 1 | | | | | | |
| 2 | $CH_3CH_3$ | Ethane | 1 | $CH_2{=}CH_2$ | Ethene | 1 | $HC{\equiv}CH$ | Acetylene | 1 |
| 3 | $CH_3CH_2CH_3$ | Propane | 1 | $CH_3CH{=}CH_2$ | Propene | 1 | $HC{\equiv}CCH_3$ | Propyne | 1 |
| 4 | $CH_3(CH_2)_2CH_3$ | Butane | 2 | $CH_3CH_2CH{=}CH_2$ | Butene | 4 | $CH_3C{\equiv}CCH_3$ | Butyne | 2 |
| ... | | | | | | | | | |
| 40 | $C_{40}H_{82}$ | | Large | $C_{40}H_{80}$ | | Large | $C_{40}H_{78}$ | | Large |

In general, the products of the chemical reaction of Equation 28 have higher enthalpy or energy of formation than the reactants, which will be described in more detail below in reference to FIGS. 5A-5B. This higher energy corresponds to the energy balance, where the energy added to the plasma is stored in higher order chemical bonds and endothermic reactions are favored by high energy transition states.

The stoichiometry balance of the reaction can be determined based on a measured composition of the outgoing and/or returning drilling fluid. Drilling fluid composition is measured as the fluid exits the wellbore—hydrocarbon concentrations are measured as are types and volumes of evolved gasses. The composition of the drilling fluid pumped downhole (outgoing fluid) is either measured as circulates back downhole, or the measured composition of the drilling fluid returned to the surface is set as the drilling fluid concentration when that mud recirculates into the wellbore. In either case, component concentrations of the initial, outgoing drilling fluid are differentiated such as by subtraction from component concentrations of the final, returning drilling fluid, which generates the change in concentration for various species occurring downhole.

Figure 5A:
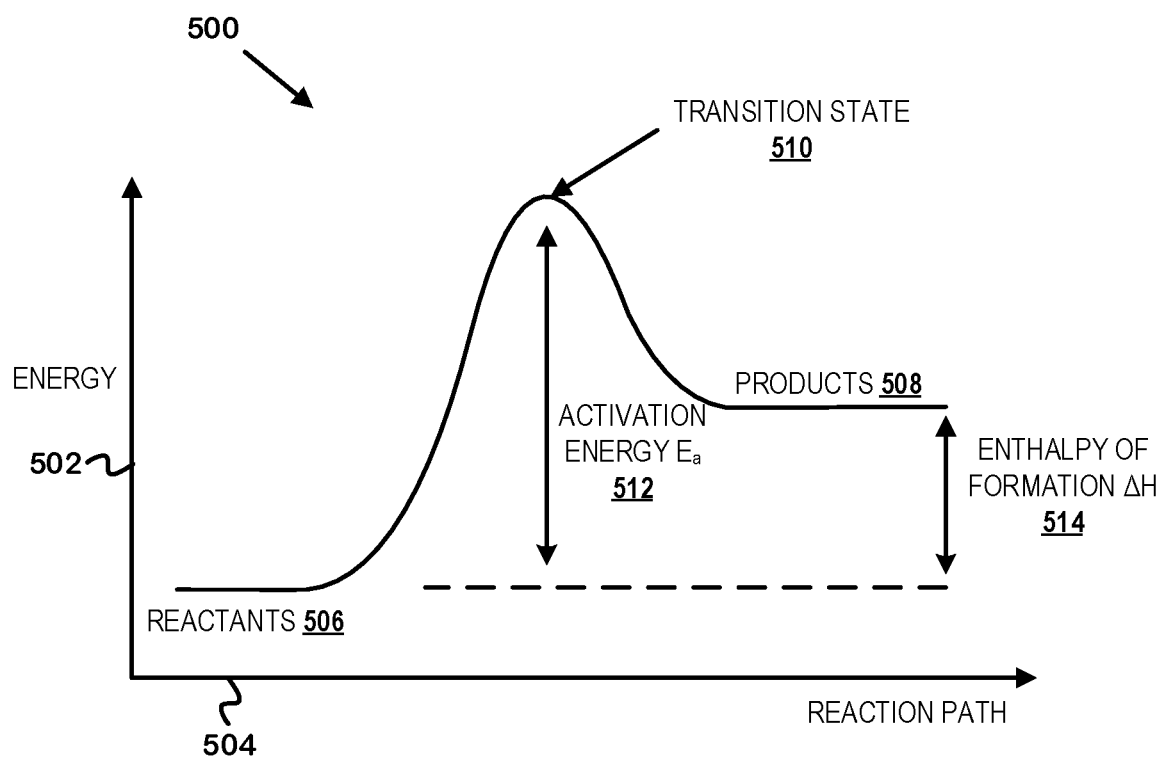
FIG. 5A depicts an example line graph of the reaction kinetics and reaction path of an example plasma-mediated chemical reaction, according to one or more embodiments.

To help illustrate, FIG. 5A depicts an example line graph of the reaction kinetics and reaction path of an example plasma-mediated chemical reaction, according to some embodiments. In particular, FIG. 5A depicts a graph 500 having a y-axis for energy 502 and an x-axis for a reaction pathway 504. Graph 500 depicts example reaction kinetics and molecular energies for example reactants and products of a pulse plasma. The plasma energy, which is the energy added to the system consumed to generate the plasma, can create highly energized particles, both kinetically energized and energized electronically above the ground state. Energized molecules and atoms therefore interact more frequently and can form transition states favorable to reaction. The graph 500 depicts an example reaction pathway (also known as a reaction path) for a set of reactants, their intermediate transition state, and the final products of the example reaction. Activation energy $E_a$ 512 is the energy per set of reactants or per reaction needed to reach transition state 510, where transition state 510 is a complex formed between the atoms of the reactant molecules that is the highest energy state during the chemical transformation from the reactant species to the product species.

For most of the hydrocarbon reactions occurring in plasma, reaction products 508 will have a greater enthalpy of formation 514 than reactants 506 (i.e., higher energy 502). Enthalpy of formation is a measure of the energy contained within a molecule as a sum of the energies contained within the chemical bonds between the constituent atoms. The plasma energy can be defined as the total energy in the plasma. The plasma energy added to the fluid is stored in higher order carbon bonds. Each molecular reaction can store the enthalpy of formation 514 (as an amount of energy) within reaction products' 508 chemical bonds. The reaction energies include activation energy $E_a$ 512 and enthalpy of formation 514, can be defined as the energy needed for a set of reactants 506 to reach transition state 510 or stored in reaction products 508. The reaction energy can be measured on a per reaction or molar basis. When species collide and react, the frequency at which transition state 510 arrangement of the hydrocarbon is reached is a function of the kinetic energy added to the molecule through absorption of a photon, stabilized via hydroxyl, or other catalysis processes. In a plasma, the kinetic energy of the particles is high because the plasma energy is high. The plasma energy is a measure of the kinetic energy of the particles and molecules within the plasma, and higher energy transition states are allowed (and occur more frequently), as shown along reaction pathway 504.

In graph 500, reaction pathway 504 is a simplified timeline of the reaction, going from reactants 506 to reaction products 508 (showing an intermediate step—the transition state 510). Reaction mechanisms, which include possible reaction pathways and intermediate steps, can be much more complicated. A reaction mechanism can be defined as the series of steps and chemical rearrangements that occur during a reaction at a molecular level, where reactants transform into products. A reaction mechanism may include intermediate steps, some of which can lead to formation of multiple different reaction products. A reaction path or reaction pathway can be defined as the method or steps of the reaction mechanism which lead from a set of reactants to a set of reaction products. A reaction can have more than one pathway that generates identical reaction products from reactants (as explained with reference to FIG. 5B), and each pathway can have a different activation energy and reaction rate. For instance, catalysts can stabilize transition states thereby lowering activation energies and increasing the speed of a given reaction rate, but even in catalyzed reactions a portion of the products may be generated through the higher energy uncatalyzed transition state. Reactions, including intermediate reaction steps, can also be reversible which means that a significant portion of the reaction products re-react to re-from the reactant species. Dehydrogenation reactions tend to be irreversible because the gaseous reaction products quickly dissociate from the hydrocarbon species, but transition states in dehydrogenation reactions are likely to form reaction products or to re-form reactants.

Plasma energy (of the entire plasma) and reaction energy (of each individual chemical reaction) can be correlated—higher plasma energy favors reactions with larger activation energies and greater enthalpy of formation. The concentration of product species multiplied by the enthalpy of formation of each species generates a total reaction energy for the chemical reactions within the plasma that can be compared to the plasma energy.

Figure 5B:
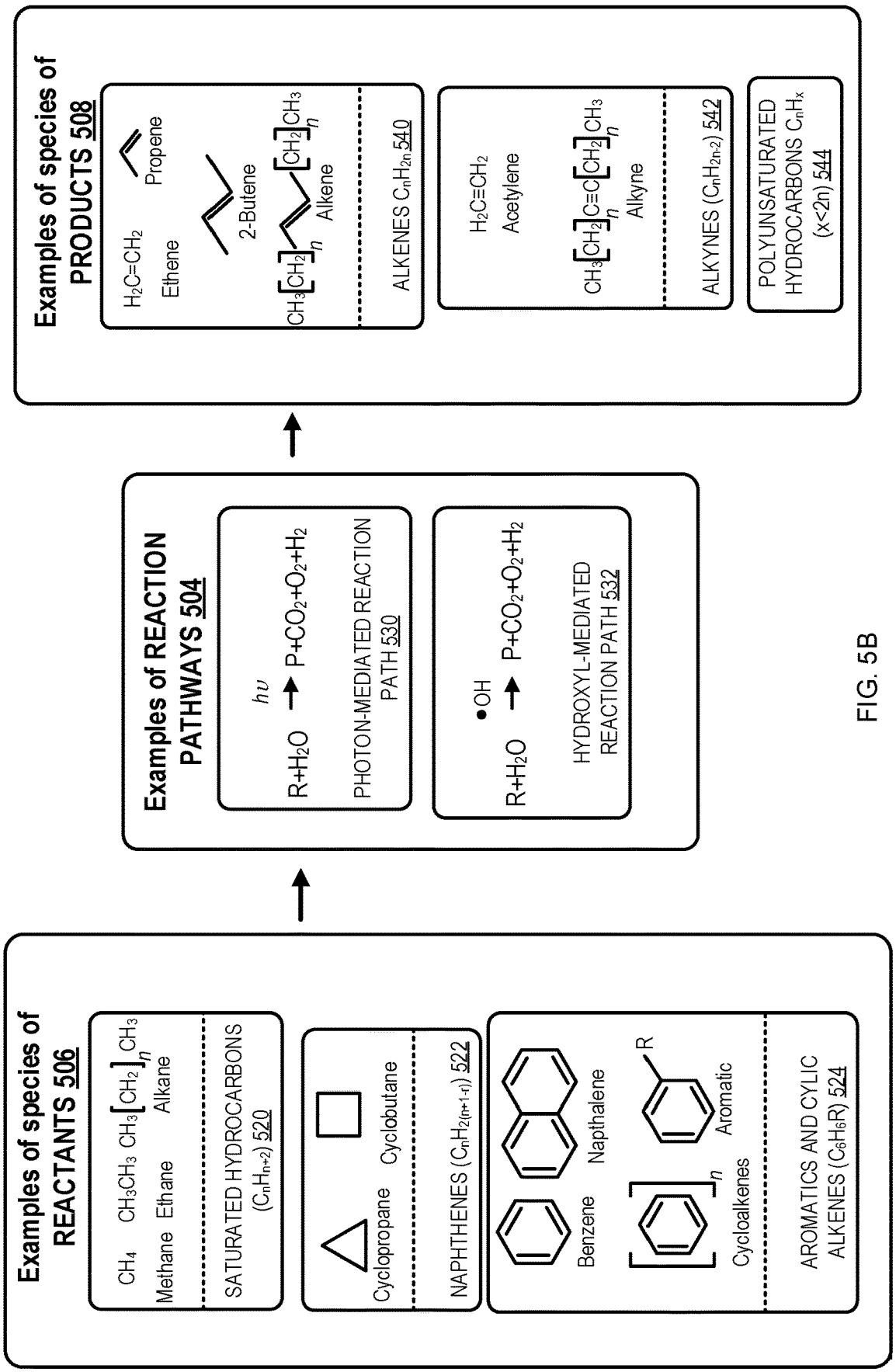
FIG. 5B illustrates example reactants and products as well as example reaction pathways, according to one or more embodiments.

To further illustrate, FIG. 5B depicts example reactants and products as well as example reaction pathways, according to some embodiments. FIG. 5B depicts examples of species of reactants 506, examples of reaction pathways 504, and examples of species of reaction products 508. To calculate the formation fluid concentration, a set of equations based on reaction rate constant and final or product concentration can be generated. For a generic product molecule, P, of the first order reaction shown in Equations 29 and 30, the final concentration [P] can be known and measured at the surface during drilling fluid analysis.

$$R \rightarrow P \qquad (29)$$

$$r = k(T)[R] = -\frac{d[R]}{dt} = \frac{d[P]}{dt} \qquad (30)$$

Where R is a generic reactant and P is a generic product of the first order reaction of Equation 29. [R] is a concentration of molecule R, [P] is a concentration of molecule [P], r is a reaction rate, and k is a reaction rate constant which is a function of temperature T.

Product species P can include at least one species from at least one of alkenes 540, alkynes 542, polyunsaturated hydrocarbons 544, and any of those species included corresponding to reactant species R. Reactant species R can include species from at least one of the alkanes or saturated hydrocarbons 520, naphthenes 522, or the aromatics and cyclic alkenes 524, as can be found in the formation fluid. If the reaction rate constant k(T) is also known, the reactant concentration [R] (which is the formation fluid concentration) for a generic product R is directly calculable according to Equation 31-33 below.

$$[P] = r*\Delta t = k(T)[R]*\Delta t \qquad (31)$$

$$[P] = \int r dt = \int k(T)[R]dt \qquad (32)$$

$$[R] = \frac{[P]}{k(T)*\Delta t} \qquad (33)$$

Where the concentrations of P and R change as the reaction occurs. Concentration changes may be large enough that the change in reactant concentrations favors the use of integrals (as shown in Equation 32) instead of discrete analysis (as shown in Equations 31 and 33). The instantaneous product concentrations may not be known, as can occur when drilling fluid circulation prevents instantaneous measurement of chemical reaction products. If the instantaneous concentrations are not known, the reaction rate and reactant concentration can be approximated using integral approximation, such as for an exponential concentration approximation, or discrete analysis.

A product molecule(s) P can be generated from a reactant molecule(s) R via an example photon-mediated reaction pathway 530 or an example hydroxyl-mediated pathway 532. The ratio between reactions catalyzed by light and those catalyzed by hydroxyl free radicals can correspond roughly to the ratio between plasma arc and plasma spark.

For the set of alkane dehydrogenation reactions (which can be considered to be the opposite of cracking reactions) encompassed by Equation 28 (set forth above), the molar concentrations of hydrogen, carbon dioxide, and oxygen gases can be determined at the surface. From the oxygen mass balance of the chemical reaction, the relationship between coefficients D, J, and K is determined, as shown in Equation 34.

$$D=2(J+K) \qquad (34)$$

Where D is the stoichiometric coefficient for water, J is the stoichiometric coefficient for carbon dioxide, and K is the stoichiometric coefficient for hydrogen as defined in the chemical reaction of Equation 28. This allows the initial concentration of water to be calculated based on the measured molar concentrations of carbon dioxide and oxygen measured at the surface, as is shown in Equation 28.

$$[H_2O]=2([CO_2]+[O_2]) \qquad (35)$$

The mass balance of the carbon and hydrogen atoms can be complicated by the multiplicity of the hydrocarbon species. The chemical analysis does not necessarily determine a concentration for each isomer of the saturated and unsaturated hydrocarbons. Isomer concentrations, where available, can refine available mass balance equations. The chemical analysis equipment can identify concentrations of hydrocarbons as a function of n and carbon to hydrogen (C/H) ratio with great specificity. The total carbon balance is given by Equation 36 and the total hydrogen balance is given by Equation 37.

$$\sum_{i=1}^{n} i*A_i + \sum_{i=1}^{n}\sum_{j=1}^{r} i*B_{i,j} = \sum_{i=1}^{n} i*E_i + \sum_{i=1}^{n}\sum_{j=1}^{r} i*F_{n,j} + \sum_{i=1}^{n} i*G_i + \sum_{i=1}^{n} i*I_i \qquad (36)$$

$$\sum_{i=1}^{n} 2(i+)*A_i + \sum_{i=1}^{n}\sum_{j=1}^{r} 2(i+1-j)*B_{i,j} + 2D = \sum_{i=1}^{n} 2(i+1)*E_i + \\ \sum_{i=1}^{n}\sum_{j=1}^{r} 2(i+1-j)*F_{n,j} + \sum_{i=1}^{n} 2i*G_i + \sum_{i=1}^{n} 2(i-1)*I_i + 2L \qquad (37)$$

Again, the stoichiometric coefficients for each of the hydrocarbon species (i.e. $A_n$, $B_{n,r}$, $E_n$, $F_{n,r}$, $G_n$ and $I_n$) come from Equation 28 previously and represent the total equation mass balance for each of the carbon species with n carbons.

The stoichiometric coefficients for the hydrocarbon species—$A_n$, $B_{n,r}$, $E_n$, $F_{n,r}$, $G_n$ and $I_n$—appear in both the carbon mass balance and the hydrogen mass balance (which also includes coefficients D and L). The stoichiometric coefficient D, J, and K are related based on the oxygen balance previously discussed in relation to Equations 34 and 35. The stoichiometric coefficients are constrained by these equations, which becomes a solvable system of equations for coefficients of the reaction.

The final concentrations of species can also be known, where [$CO_2$], [$O_2$], [$H_2$] can be measured directly. If not, all water is consumed during the plasma-driven chemical reaction, the initial concentration of water can be calculated directly from the gaseous product concentration and the final concentration of water in the drilling fluid, given by Equation 38.

$$[H_2O]_{initial}=[H_2O]_{final}+2([CO_2]_{final}+[O_2]_{final}) \qquad (38)$$

Where initial denotes the concentration in the formation fluid and drilling fluid downhole before the plasma reaction, and final denotes the concentrations measured in the drilling fluid after the reaction (either at the surface or with analysis equipment downhole). If the drilling fluid contains water when it is pumped downhole, the formation fluid's water concentration can then be given by Equation 39, which accounts for a change in water concentration due to formation fluid influx.

$$[H_2O]_{initial} = \Delta[H_2O]_{drilling\ fluid} + 2([CO_2]_{final} + [O_2]_{final}) \quad (39)$$

Where the change in drilling concentration in the drilling fluid is represented by A, which is the change in the water concentration measured in the drilling fluid before and after the reaction.

Product hydrocarbon concentration $[C_nH_{2n+2}]$, $[C_nH_{2(n+1-r)}]$, $[C_nH_{2n}]$, and $[C_nH_{2n-2}]$ can also be known. The known and unknowns together create a system of equations where the initial formation concentrations are solvable. Further, reaction kinetics allow refining of the concentrations based on known product concentration and calculable reaction rates, as shown in Equations 24-25 (set forth above).

If reaction rates are known (i.e. can be calculated based on product concentrations as a function of time) and the reaction order of the rate limiting step (i.e. first order, second order, etc.) is known, then exact concentrations of reactants are calculable from product concentrations. For hydrocarbon dehydrogenation, most reaction rates are first order or zeroth order. Zeroth order reactions depend on time, not on reactant concentration (to a first approximation). Product concentrations follow Equation 40.

$$[P] = k(T) * \Delta t \quad (40)$$

Where [P] is the concentration of a generic product molecule P and $\Delta t$ is the lifetime of the reaction. These types of reaction kinetics correspond to chemical reactions dependent on free radicals, equilibrium rearrangement at high temperature (such as for hydrocarbon isomers in equilibrium), and for catalyzed reactions where k may be zeroth order with respect to reactants but depend on the concentration of a catalyst. For first order reactions, product concentrations can be related to reactant concentrations as shown in Equation 41.

$$[P] = k(T)[R] * \Delta t \quad (41)$$

Where [R] is the concentration of a generic reactant molecule R. Where the concentration of R is also a function of time, this equation becomes $$[P] = \int k(T)[R] dt \quad (42)$$

In general, the concentration of a first order reactant as a function of time is given by solving the rate equation to get Equation 43, below:

$$[R] = [R]_0 e^{-k(T)*t} \quad (43)$$

Where $[R]_0$ is the initial concentration of generic reactant R, k(T) is the reaction rate constant, and t is time. Substituting Equation 43 into Equation 42 yields equation 44:

$$[P] = \int k(T)[R]_0 e^{-k(T)*t} dt = k(T)[R]_0 \int e^{-k(T)*t} dt = [R]_0 e^{k(T)*t} \quad (44)$$

Where this relationship holds when one molecule of reactant R yields one molecule of product P. The product concentration for first order reactions can be similarly related to reactant concentrations for different stoichiometric relationships as well.

By correlating reaction rate constant to temperature and plasma power, rate constant values are further refined. The rate constant for a plasma reaction can be a function of temperature, plasma power, and activation energy. Activation energy for transition states are known. Determination of a reaction rate constant for a first order reaction can be made by varying the plasma power (where temperature is constant, and activation energy is a function of the transition state and therefore constant for the specific reaction mechanism). This is shown in Equations 45-47, below, where the reactant concentration [R] is a function of the formation and does not vary over the time scale of the power analysis.

$$[P]_1 = k(T, PW_1)[R] * \Delta t = [R]_0 e^{k(T,PW_1)*t} \quad (45)$$

$$[P]_2 = k(T, PW_2)[R] * \Delta t = [R]_0 e^{k(T,PW_2)*t} \quad (46)$$

$$\frac{[P]_1}{[P]_2} = \text{Exp}[k(T, PW_1) - k(T, PW_2)] = f\left(\text{Exp}\left(\frac{PW_1}{PW_2}\right)\right) \sim f(PW) \quad (47)$$

Where P represents the product concentration and PW represents the plasma power. PW is used so that power is not confused with either product concentration [P] or pressure as used previously. Subscripts 1 and 2 denote a first power setting its corresponding concentrations, temperature, and time, and a second power setting its corresponding concentrations, temperature, and time. T is temperature and t represents time. The power analysis can be simplified if all time and temperatures remain constant while power is varied, so that the relationship between k(T) and power can be explored.

The dependence of the rate constant on plasma power can be determined from the product concentrations as a function of power. Once the relationship between rate constant k and plasma power is known, then the relationships between reactant concentration and product concentration can generate another set of equations that further restrict the degrees of freedom of the system.

The reaction rate constants can also vary by plasma type. For example, the reaction rate constants for plasma arcs can be different than the reaction rate constants for plasma sparks even for similar products and reactants over the same rate limiting step. Certain reaction products are favored by different types of plasma, as previously discussed in relation to hydroxyl free radical formation and hydroxyl mediated versus photon mediated reaction pathways. Reaction rate constants for each type of plasma can be determined via at least one of a plasma power analysis or a spark versus arc ratio analysis.

The relationship between the product and reactant concentrations can thereby be constrained enough to allow for solving for reactant concentrations based on measured product concentrations and plasma parameters. These solutions can be determined directly, with sufficient product information, or can be solved iteratively or by machine learning applied to a body of data.

Returning to operations of FIG. 4B at block 419, the fluid loss or influx is estimated based on the concentration of species in the drilling fluid. Influx of formation fluid into the wellbore or loss of drilling fluid to the formation can be further determined based on the ratio of plasma reaction products. For example, with reference to FIG. 1, computer 162 can perform this estimation. Computer 162 can determine a ratio between hydrogen and small molecular weight hydrocarbons or between hydrogen and aromatics or between small molecule alkanes and aromatics in order to estimate the amount of drilling fluid lost to the formation or the fluid volume gained due to an influx of formation fluids. Computer 162 can also estimate the total volume of drilling fluid returned to the surface using instrumentation 161 or fluid reconditioning system 142.

Drilling fluid or mud is necessary to maintain pressure downhole above the pore pressure of the formation. If the pressure downhole is below the pore pressure of the formation, the pressure downhole can be considered too low as gas and fluid can enter the wellbore from the surrounding formation. For reactive gases like $H_2$ and $H_2S$, entrance of dissolved gasses into the drilling fluid can lead to corrosion downhole and can lead to violent or explosive evolution as the drilling fluid moves towards lower pressures at the surface. If the pressure downhole is above the formation fraction pressure, the pressure downhole can be considered too high as the wellbore or wellbore walls may collapse as the formation is fractured or destroyed by drilling fluid forces into weaker strata. Monitoring the amount or volume of drilling fluid returned to the surface allows mud logging to estimate the influx of fluid into the wellbore or the loss of fluid to the formation. Pulse power drilling can complicate this determination because the chemical reactions downhole generate gaseous products, in addition to vaporization of water (from aqueous fluids) and carbon dioxide and the like dissolved in hydrocarbon fluids. Many of the gasses generated downhole via the plasma will dissolve, under pressure, back into the drilling fluid (which can be assumed to be a non-Newtonian high temperature and high-pressure fluid) as the plasma is quenched. The gaseous products are detectable via low pressure or low temperature gas extraction, or distillation, from the drilling fluids.

Further, influx and loss can be detected by a shift in the chemical composition of the drilling fluid, or product concentrations in the drilling fluid. When drilling fluid is lost to the formation, that loss can result in a steadier drilling fluid chemical composition. The drilling fluid returned to the surface can significantly match the composition of the drilling fluid that was pumped downhole. The loss to the formation limits the amount of hydroxyl free radicals created from water molecules available to catalyze the chemical reactions downhole, and therefore slows reaction rates.

In the case of an influx into the wellbore, formation fluid and product concentration in the drilling fluid can increase. Saltwater flow into the wellbore can significantly increase the amount of hydrogen gas detected at the surface. The ions present in the saltwater increase the fractional ionization of the plasma formed downhole. The increase in hydroxyl groups (where water readily decomposes into hydroxyl groups and hydrogen) can increase reaction rates, but significantly increases the production of hydrogen molecules at a rate greater than the increase for other products. An influx of gas from the formation increases the concentration of methane and short carbon products. Hydrocarbon gas is already heavy in small molecular weight carbon species (i.e. approximately n≤10), and these reactants tend to crack and form small unsaturated molecules or merge but remain small in the presence of catalyst. An influx of oil from the formation, where oils contain high molecular weight hydrocarbons, can lead to an increase in the complex, aromatic, and unsaturated product species and concentrations.

The total volume of drilling fluid or drilling fluid level in the mud pit remains a valuable method of measuring formation loss and influx. However, monitoring the products of the chemical reactions downhole enable mud logging to further record information about the formation fluid.

At block 420, the estimated formation fluid concentrations are refined by correlating reaction rates to plasma energy. Reaction rate calculations can be applied in order to generate additional equations to better define the system of linear equations to generate a definite solution. For example, with reference to FIG. 1, computer 162 can perform this operation. Many of the reaction pathways can share transition states, where transition states determine the activation energy $E_a$ of a reaction pathway. For reactions with known activation energy, the reaction rate constant can be calculated directly from the measured temperature at the plasma (based on the Arrhenius or similar equation) or can be estimated based on a plasma power analysis performed in the wellbore previously.

Free radicals are high energy and unstable, especially in alkanes. The hydroxyl radical has the longest lifetime of the free radicals produced downhole. The chemical reactions occur at equilibrium in the plasma, where high velocity electrons enable formation of transition states. For photon-emitting plasmas, photons can generate excited states inside the plasma and in surrounding fluid. Without regard to which excitation mechanism generates the transition state, products are generated as the plasma is quenched and further chemical transitions become energetically unfavorable.

Further information is gained via periodic off bottom plasma generation events. The drilling bit is retracted from the wellbore bottom and suspending in the wellbore surrounded by drilling fluid (or only partially introduced into the well) and a plasma is generated, the contribution of the drilling fluid to the reaction rate and product species is then measured. The drilling fluid plasma products is then subtracted from the total product concentration measured at the surface, in order to selectively identify the reaction products corresponding to the formation and formation fluid at the wellbore bottom. The off bottom analysis can also be conducted for a variety of plasma powers, in order to determine the arc vs. spark ratio of each plasma power setting which can be extrapolated as the arc vs. spark ratio for the wellbore bottom plasma in the formation.

At block 422, an arc to spark ratio is calculated based on concentrations, gas species, and volume of the drilling fluid. In particular, a ratio between the plasma power that generates the plasma arc and the plasma power that generates any plasma sparks is calculated. For example, with reference to FIG. 1, computer 162 can make this calculation. This ratio may be calculated as a fraction, a percentage, or a range. The ratio between the arc and spark for the plasma can depend on the power used to generate the plasma and upon wellbore geometry and dielectric characteristics. As discussed in reference to FIG. 3A-3C, both porosity and permeability along with formation fluid resistivity can contribute both to the total dielectric strength between the anode and cathode and to the distribution of plasma arcing vs. sparking. Plasma arcs and plasma sparks can produce distinctive products and the ratio of these products can correspond to the ratio between the plasma arc and spark. For instance, plasma sparks generate high temperature, more spherical plasma, and vapor bubbles in fluid. Whereas, plasma arcs generate lower temperature, more elongated bubbles with longer lifetimes. Certain species, for example are preferentially formed in each type of plasma. For example, plasma sparks favor formation of hydroxyl catalyzed reaction and produce a significant amount of hydrogen. Whereas, plasma arcs favor photon catalyzed reactions, where ultraviolet (UV) photons especially promote carbon-carbon bond formation especially cyclic alkanes (naphthenes).

Figure 6A:
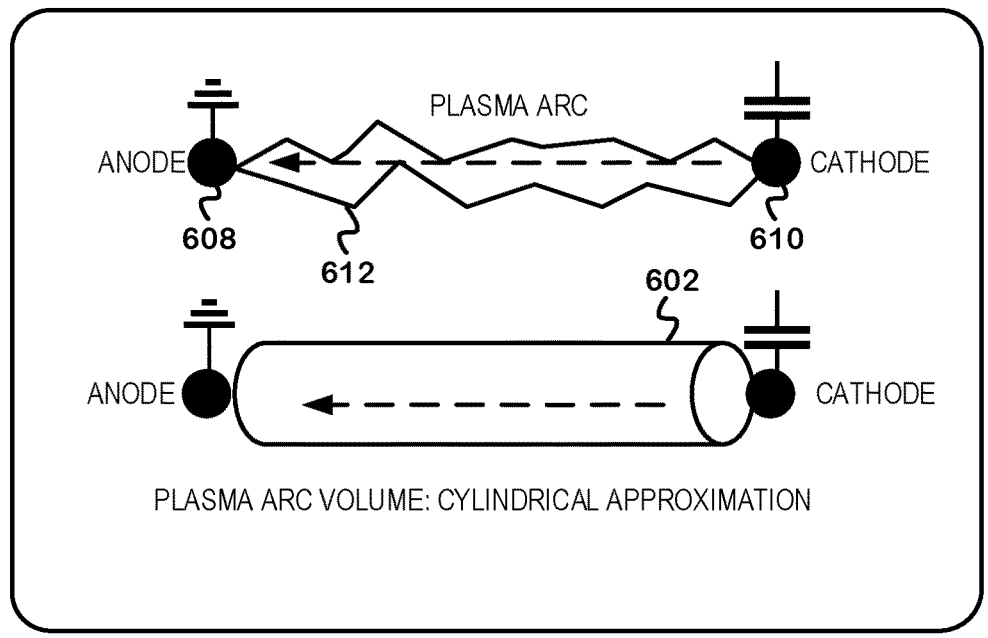
FIG. 6A depicts the geometric approximation for a plasma arc, according to one or more embodiments.
Figure 6B:
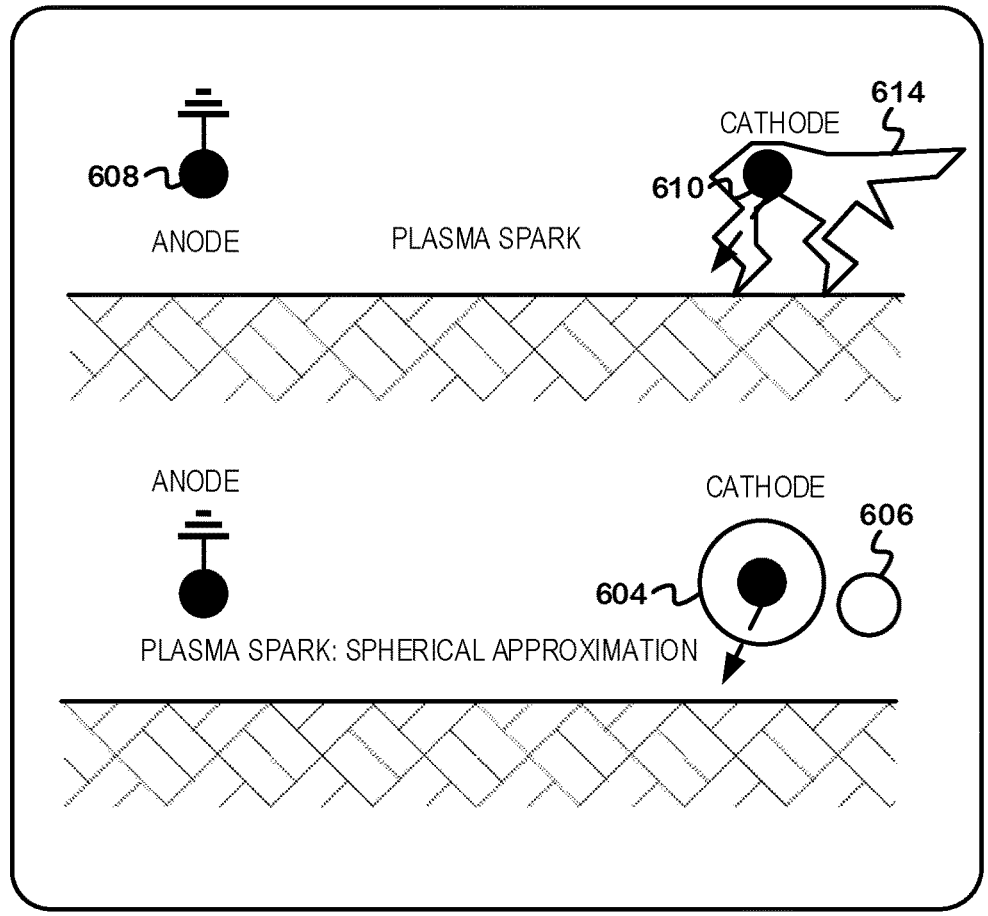
FIG. 6B illustrates the geometric approximation for a plasma spark, according to one or more embodiments.

To help illustrate, FIGS. 6A-6B depict example geometric approximations for a plasm arc and a plasma spark, respectively. FIG. 6A depicts the geometric approximation for a plasma arc, according to one or more embodiments. FIG. 6A depicts a plasma arc 612 between an anode 608 and a cathode 610. Plasma arc 612 may be generated as DC plasma discharges between anode 608 and cathode 610. As shown, plasma arc 612 appears as jagged emissive paths as the DC plasma discharges. AC plasma discharges tend to have a softer more even glow and are usually contained by a magnetic field. Plasma arc 612 is visible because highly energetic electrons and molecules are created, which emit photons as they decay back to their ground states.

Within a plasma, particles can be so energetic that chemical bonds are in flux. The chemical composition of ions and molecules can be set when they leave the plasma, either because the plasma is quenched, or because their kinetic energy takes them outside of the plasma bounds. In either case, the chemical reactions can occur at the boundaries of the plasma where each species no longer experiences the excitation or collisions for it to reach a transitional state (as explained with reference to FIGS. 4A-4B above). The chemical reaction rates for formation of complex hydrocarbons from alkanes and naphthenes (as described in Equation 22) can depend most closely on the concentration of hydroxyl radicals and on energetic photons, both of which function as catalysts for such reactions. As depicted in FIG. 6A, plasma arc 612 can be approximated as a cylinder 602 sustained by electrons from anode 608 to cathode 610 and generate larger, elongated gas-phase bubbles.

FIG. 6B depicts the geometric approximation for a plasma spark, according to one or more embodiments. FIG. 6B depicts a plasma spark 614 between anode 608 and cathode 610. Plasma spark 514 can be generated as a DC plasma discharges between anode 608 and cathode 610. As shown, plasma spark 614 appears as a jagged branching path surrounding cathode 610. Plasma spark 614 can represent the plasma generated that does not complete the circuit between anode 608 and cathode 610. Plasma spark 614 is visible because, as for the plasma arc, highly energetic electrons and molecules are created, which emit photons as they decay back to their ground states. Plasma spark 614 tends to generate spherical bubbles 604, 606 as a result of hydrodynamics.

Each type of plasma also trends towards a different plasma temperature. Plasma arcs have lower electron temperatures than plasma sparks, where plasma sparks have higher electron kinetic energy because more energy is required to create a plasma in the absence of the strong electric field between the anode and cathode. The individual reactions occurring in each type of plasma can be the same, but the dominant reaction mechanisms can differ as a result of differences in surface area and temperature.

Returning to FIG. 4B at block 426, the plasma energy and reaction rate estimates and calculations are updated based on the arc to spark ratio. For example, with reference to FIG. 1, computer 162 can perform this update. The arc to spark ratio can estimated and updated, along with the other reaction and plasma parameters, until the stoichiometric equations balance and concentrations of formation fluid species are determined. Computer 162 can determine the reactant concentrations exactly or to within a preselected error range. Such a determination can involve an iteration of all factors, multiple iterations, look up of reaction rate constants based on plasma power, or based on machine learning. Computer 162 can maintain a record of the drilling fluid species concentration before and after the plasma is applied (i.e. before the mud is pumped downhole and then at the surface) in order to correctly account for species in the drilling fluid, species in the formation fluid, and the species that are reactants in the plasma chemical reaction (measured as chemical products).

At block 428, the electrical properties of the formation at the drill bit are determined. For example, with reference to FIG. 1, computer 162 can make this determination based on the determination of the formation fluid (found in the pore spaces), the arc versus spark ratio, and the plasma power lost to the formation. The electrical properties of the dielectric, including breakdown voltage and resistivity, can correlate to fluid and rock properties.

At block 430, the formation permeability is determined based on the porosity determined at block 412 and the electrical characteristics of the formation fluid and formation calculated at block 428. For example, with reference to FIG. 1, computer 162 can make this determination. The permeability can be defined in terms of the interconnectedness of the pore spaces, or pore throat size or pore diameter, and in relation to the pore volume.

Permeability is a measure of the formation's or formation strata's ability pore connectivity or ability to transmit fluids and is an important petrophysical property. The permeability of a formation effects the dielectric constant of the combined drilling fluid, formation fluid, and rock. The permeability of the formation correlates to the arc to spark ratio, where interconnected pores (which are more permeable) are also more conductive. High permeability formation layers can bias arc formation, where the connection between the anode and cathode and current transport between them happens preferentially in the pore spaces. Interconnected pores can provide a conductive (or more conductive) path for electrons, over which the breakdown voltage will be reached more quickly and where the plasma will form. Low permeability rocks, where pores are not connected or with smaller pores, will preferentially form sparks where there is no free electron path between the anode and cathode. Charge carriers in fluids are intrinsically more mobile than charge carriers in solids, especially ionic solids and insulators.

The combination of porosity and permeability determination allow rock formation type determination. Formation layer type can be determined based on lithology related to formational fluid, rock porosity, and permeability or can be determined based on the characterized formation information based on machine learning or discrete analysis.

At block 432, the formation and formation fluid are determined as a function of depth. For example, with reference to FIG. 1, computer 162 can determine the types of formation and formation fluid type based on one or more of porosity, permeability, electrical characteristics, and formation fluid composition. Computer 162 can also correlate plasma and chemical parameters to formation layers identified at the depth of the drill bit. Computer 162 may output a mud log analogous to those obtained for traditional mechanical drilling or may additionally output plasma parameters and major product species as a function of depth.

Figure 7:
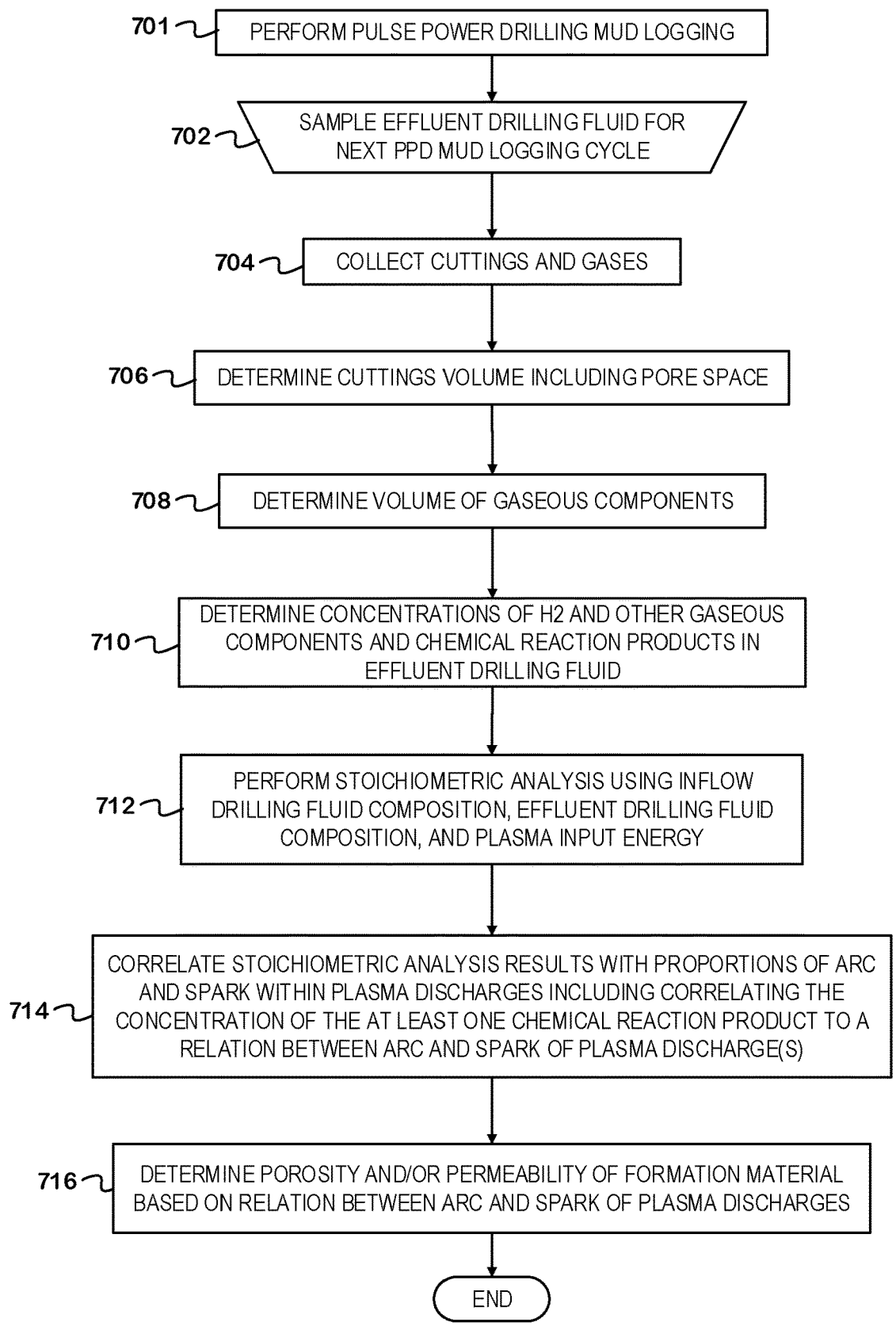
FIG. 7 depicts a flowchart of example operations for determining porosity and permeability based on a plasma chemistry derived relation between arc and spark for pulse power drilling, according to one or more embodiments.

B. Example Operations for Determining Porosity and Permeability of Formation Material Based on a Plasma Chemistry Derived Relation Between Arc and Spark for Pulse Power Drilling FIG. 7 depicts a flowchart of example operations for determining porosity and permeability based on a plasma chemistry derived relation between arc and spark for pulse power drilling, according to one or more embodiments. Embodiments of the example operations described and illustrated in the flowchart 700 of FIG. 7 may include operations that are performed by a pulse power analysis system 100 as illustrated and described with respect to FIG. 1 and described in blocks 412 and 430 of FIG. 4B. However, program code naming, organization, and deployment can vary due to arbitrary programmer choice, programming language(s), platform.

FIG. 7 describes a method for determining porosity and/or permeability of formation material based on correlating concentrations of chemical species, particularly gasses, produced downhole with a relation between arc and spark, such as a qualitative and/or quantitative relation between arc and spark. Following one or more discharges of an electric pulse downhole during pulse power drilling, plasma arc and/or plasma spark can be generated as a result of an interaction between the electric pulse and downhole fluids, including drilling fluid. Gaseous species (e.g. hydrocarbon species, hydrogen, carbon dioxide, etc.) can be formed as chemical reaction products at the interface of bubbles associated with generation of plasma arc or plasma spark. The bubbles produced by plasma arcs and plasma sparks exhibit differing characteristics. Referring to FIGS. 6A-6B, plasma arcs tend to generate lower temperature, elongated or cylindrical bubbles with longer lifetimes which are smaller in size (i.e., in terms of volume), while plasma sparks generally produce high temperature, spherical bubbles. Certain species are preferentially formed in each type of plasma. Plasma sparks favor formation of hydroxyl catalyzed reactions and produce a substantial amount of hydrogen, while plasma arcs favor photon catalyzed reactions, where ultraviolet (UV) photons especially promote carbon-carbon bond formation, particularly cyclic alkanes (naphthenes). Plasma arc and plasma spark are thus associated with both different ratios of gaseous species of interest appearing as products as well as bubble types. The concentration of the gaseous species determined from analyzing drilling fluid returning to the surface and/or approximations of bubble volume can therefore be correlated with a relation between plasma power which generates plasma arc and plasma power which generates plasma spark, or the relation between arc and spark. For example, the relation between arc and spark may be a ratio of arc to spark or a ratio of spark to arc. While the example operations refer to such a ratio of arc to spark as an example of the relation between arc and spark, the relation between arc and spark may be represented with different quantitative and/or qualitative relations among implementations.

At block 701, pulse power drilling mud logging is performed. The pulse power drilling mud logging can be performed as depicted in flowcharts 400-450 of FIGS. 4A-4B or can be performed in an alternate manner. The pulse power drilling mud logging can measure formation fluid as a function of time, which is related to drilling depth in the wellbore via the circulating drilling mud, and provides information about the chemical composition of drilling fluid which has interacted with an electric pulse emitted from the drill bit of the drill string.

At block 702, a next PPD mud logging cycle begins with a series of operations for collecting and analyzing effluent drilling fluid samples to determine porosity and/or permeability of formation material proximate the drill bit. The cycle beginning with block 702 may be performed over a specified time interval or drilling depth interval during with the PPD drill bit emits plasma discharges during drilling. At block 704, the system collects cutting and gasses from the returning effluent drilling fluid. For example, extraction system 144 and fluid reconditioning system 142 may be utilized to collect the cuttings and gasses. At block 706, the system determines the total volume of cuttings material including internal pore space. For example, an estimate of cuttings volume may be obtained based on the borehole area and depth drilled over a specified interval.

At block 708, a volume of gas formed as bubbles produced downhole as a result of generating plasma arc and/or plasma spark following emission of an electric pulse is approximated. For example, with reference to FIG. 1, the computer 162 can make this approximation. When an electric pulse is discharged, plasma and vapor bubbles can be produced as downhole fluids are vaporized and converted into a high-pressure vapor/gas. The volume of gaseous species generated downhole can be calculated using Wilson's model or another non-ideal gas approximation, depicted above as Equation 2, as described in reference to FIG. 3B. The volume of the gaseous species can then be leveraged to model an approximation of bubbles produced downhole in terms of volume and/or surface area. This approximation can be determined based on known geometries of bubbles typically associated with each of a plasma arc and a plasma spark (i.e., geometries of cylinders and spheres, respectively), a distance between the anode and cathode of the drill bit, and/or the volume of gaseous species determined using Equation 2. A radius of the bubble(s) may also be approximated based on a plasma power analysis and/or based on pulse power drilling parameter settings for pulse width.

At block 710, concentrations of gaseous species produced downhole are determined. For example, with reference to FIG. 1, the computer 162 can perform the determination. The concentrations of gaseous species, such as hydrocarbon species, hydrogen, etc., may have been previously determined during pulse power drilling mud logging operations performed at block 701. For instance, the identities and concentrations of hydrocarbon or other gaseous species appearing as products of the reaction occurring as a result of emitting of an electric pulse may have been determined based on analysis of the chemical composition of drilling fluid as described in reference to FIGS. 4A-4B at blocks 408, 414, and 416. In addition, concentrations of non-gaseous chemical reaction products may be determined. Identities and concentrations of chemical reaction products can be identified based on analysis of a chemical composition of drilling fluid which has interacted with an electric pulse emitted from the drill bit of the pulse power drill string.

At block 712, the system performs stoichiometric analysis based on inflow drilling fluid composition, effluent drilling fluid composition, and plasma input energy as described with reference to FIGS. 4A and 4B. At block 714, the concentration of the at least one chemical reaction product is correlated to a relation between a plasma arc and a plasma spark of the plasma discharge. For example, with reference to FIG. 1, the computer 162 can perform the correlation. The concentration of the at least one chemical reaction product can be correlated with a relation between plasma arc and plasma spark because the reactions associated with plasma arc and plasma spark result in formation of different products, as some products will be present in higher concentrations when plasma arc is generated and others will be present in higher concentrations when plasma spark is generated. As depicted and described in FIG. 8, the plasma energy may be adjusted based on energy lost to the formation. Approximations of a volume of bubbles produced as a result of the reaction downhole may also inform the correlation to the relation between plasma arc to plasma spark because plasma arc and plasma spark produce bubbles with different characteristics. For instance, as described above, plasma arc tends to generate elongated, cylindrical bubbles, while plasma spark generally produces spherical bubbles. The relation between arc and spark can subsequently be evaluated to determine updates to drilling parameters for drilling of the borehole with the pulse power drill string. The relation between arc and spark can also be leveraged to perform an evaluation of formation and drilling fluid, such as to determine one or more properties of the formation surrounding the borehole.

At block 714, the concentrations of gaseous species and/or bubble volume approximations are correlated with a relation between plasma arc and plasma spark. For example, with reference to FIG. 1, the computer 162 can perform this correlation. The relation between plasma arc and plasma spark generated as a result of discharging the electric pulse can indicate relative degrees to which the plasma power input generated plasma arc and plasma spark. For instance, the relation may be represented as a fraction, a percentage, or a range. The relation between the arc and spark for the plasma can depend on the power used to generate the plasma and upon wellbore geometry and dielectric characteristics. As discussed in reference to FIGS. 3A-3C, FIGS. 4A-4B, and 5A-5B, both porosity and permeability along with formation fluid resistivity can contribute both to the total dielectric strength between the anode and cathode and to the distribution of plasma arcing and sparking. Because the reactions associated with plasma arc and plasma spark result in formation of different products, where some products will be of a higher concentration when plasma arc is generated and others will be in a higher concentration when plasma spark is generated, the concentrations of the gaseous species produced downhole can be correlated with a relation between arc and spark. For instance, plasma sparks favor formation of hydroxyl catalyzed reaction and produce a significant amount of hydrogen, while plasma arcs favor photon catalyzed reactions, where ultraviolet (UV) photons promote carbon-carbon bond formation, particularly cyclic alkanes (naphthenes). By determining the ratio of the products based on the analysis of the fluids and from knowledge about their formation rates, the concentrations of gaseous hydrocarbon species appearing as products can be correlated with a relation between arc and spark based on a ratio of these species identified in the products. As an example, the ratio of products associated with plasma arc to products associated with plasma spark which are identified from analysis of drilling fluid may be 4:1 and can thus be correlated with a relation between arc and spark expressed as a ratio of 4:1, or 80% plasma arc and 20% plasma spark. Because bubbles formed as a result of plasma arcs and plasma sparks have different characteristics, the model approximation of bubbles determined at block 708 can be correlated with the relation between plasma arc and plasma spark alternatively or in addition to the concentrations. For instance, the surface area and/or volume of the bubble(s) can be evaluated to determine the extent to which the surface area and/or volume are indicate of plasma sparking and plasma arcing based on the known geometries of bubbles formed in each reaction.

At block 716, the system determines porosity and/or permeability of formation material based on the relation between arc and spark determined at block 714. For example, the system may determine permeability of the formation material as a function of an increasing fraction of the plasma discharge(s) that comprises arc. In some embodiments, the formation material porosity may be determined as a function of an increasing fraction of the plasma discharge that is spark. Alternative or additional supplemental information collected at blocks 702 and 704 may be used to supplement the arc and spark relation in terms of determining porosity and/or permeability. For example, the permeability of the formation material may be determined based, at least in part, on a determined porosity of the formation material cuttings collected at block 704.

Figure 8:
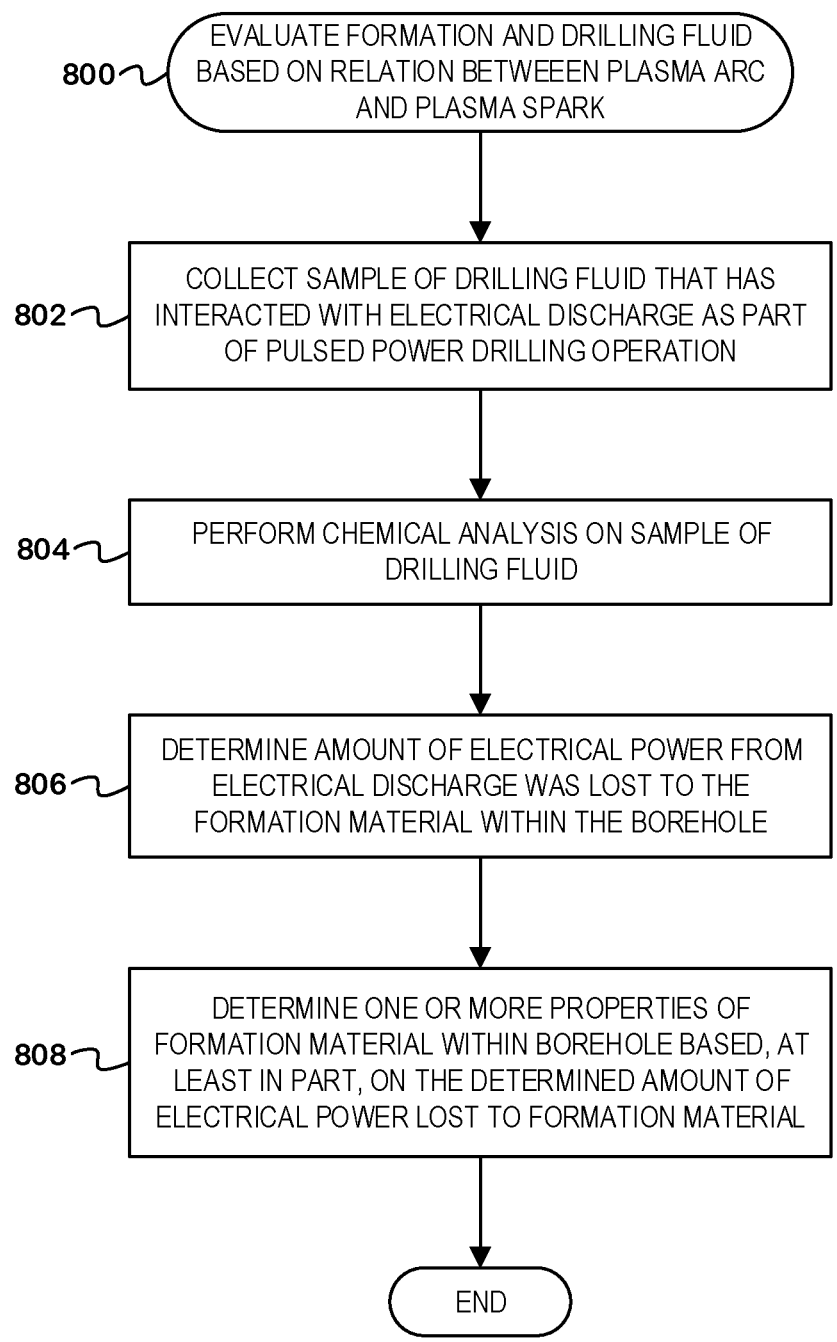
FIG. 8 depicts a flowchart of example operations for formation and drilling fluid evaluation based on a relation between arc and spark derived from chemical changes resulting from a plasma discharge, according to one or more embodiments.

C. Example Operations for Formation and Drilling Fluid Evaluation Based on Relation Between Arc and Spark Derived from Chemical Changes Resulting from a Plasma Discharge FIG. 8 depicts a flowchart of example operations for formation and drilling fluid evaluation based on a relation between arc and spark derived from chemical changes resulting from a plasma discharge, according to one or more embodiments. In various embodiments, the example operations may be performed by a pulse power drilling assembly, such as system 100 as illustrated and described with respect to FIG. 1. In various embodiments, example operations may be performed by an analysis system, such as analysis system 160, which may include on or more test instrumentation or test devices, such as illustrated and described with respect to instrumentation 161 of FIG. 1, and/or by one or more computers, such as computer 162 and/or remote computer 163 as also illustrated and described with respect to FIG. 1.

At block 802, a sample of drilling fluid is collected. The sample of drilling fluid includes a portion of drilling fluid that has been exposed to an electrical discharge generated by a pulse power drilling apparatus operating in a downhole environment. Collecting a sample of the drilling fluid may be performed at the surface, for example using the sample collection system such as extraction system 144 as illustrated and described with respect to FIG. 1. In various embodiments, collecting a sample of the drilling fluid may be performed at or near the location of the pulse power drilling assembly and in the area where the discharge of the electrical energy occurred, for example using a port 125 and a sampling tool 124 as illustrated and described with respect to system 100 and FIG. 1. Collecting a sample of drilling fluid may include correlating the collected sample of drilling fluid with one or more of a measured temperature and/or a measured pressure of the drilling fluid measured at the location and at the time of the interaction of the drilling fluid included in the sample with the electrical discharge. Sensors, such as sensors included as part of the pulse power drilling assembly, may be used to sense a temperature and/or a fluid pressure of the drilling fluid at the location and at the time when the sample of drilling fluid interacted with the electrical discharge provided by the pulse power assembly. The temperature and/or the drilling fluid pressure sensed at the time of the interaction of the drilling fluid and the electrical discharge can be correlated to the collected sample of drilling fluid. Alternatively or in addition, one or more electrical parameters, such as voltage level(s), current level(s), duty cycle(s), and waveform(s) of the electrical discharge that interacted with the drilling fluid, may be correlated to the sample of drilling fluid collected.

At block 804, a chemical analysis is performed on the sample of drilling fluid. Performing the analysis on the sample of formation fluid may include determining one or more chemical properties of the sample of drilling fluid using any of the devices and/or testing techniques described above (e.g., in reference to FIGS. 3A-3B) for testing chemical and/or physical properties associated with drilling fluid. Performing the analysis on the sample of drilling fluid may include determining one or more physical properties, such as a level and/or concentration of a gas of some type, found in the sample of drilling fluid.

At block 806, an amount of electrical power from the electrical discharge that was a lost to a formation material is determined. The electrical power loss corresponds to an electrical power loss which occurred at the time the portion of the drilling fluid corresponding to the sample of drilling fluid was exposed to the electrical discharge. The amount of electrical power loss can be determined based, at least in part, on the chemical analysis. The chemical composition and/or the level of one or more particular chemical compounds formed in the drilling fluid that has interacted with the discharge of electrical energy emitted from the electrode(s) of a pulse power drilling assembly as part of a pulse power drilling operation may be affected by the type of electrical conduction, or arcing versus sparking, that has occurred at the time of the electrical discharge from the electrode(s). As described in reference to FIGS. 3A-3B, arcing refers to a discharge of electrical power where the electrical current flows from the electrode(s) back to a cathode or ground conductor of the pulse power drilling assembly. Sparking refers to a discharge of electrical power from the electrode(s) of the pulse power drilling assembly where the electrical current leaves the electrode(s) and dissipates into the formation material and does not return to the cathode or some grounded conductor of the pulse power drilling assembly. Some portion of any given electrical discharge emitted from the electrode(s) may result in both arcing and sparking in which, for example, a portion (e.g., a percentage less than 100 percent) of the current returns to the cathode or grounded conductor of the pulse power drilling assembly, and the remainder (remaining percentage of 100 percent of the total current) is lost to the foundation. The relative amounts of arcing versus sparking associated with an electrical discharge emanating from the electrode(s) of a pulse power drilling assembly as part of a pulse power drilling operation may thus be indicated with a relation between arc and spark with which results of the chemical analysis of the drilling fluid sample can be correlated (e.g., based on identified concentrations of gasses). For instance, the relative amounts of arcing versus sparking may be expressed with a quantitative and/or qualitative relation between arcing and sparking. As an example, the relative amounts of arcing versus sparking may be expressed as a ratio of the arc to the spark or a ratio of the spark to the arc.

At block 808, one or more properties of a formation material present in the downhole environment at the location of the electrical discharge corresponding to the sample of drilling fluid are determined based, at least in part, on the determined amount of electrical power loss to the formation material. The relation between arcing and sparking may be used to determine one or more properties of the formation material present within the borehole at the location where the drilling fluid included in the sample of drilling fluid had interacted with the electrical discharge, such as a dielectric constant, breakdown voltage, and/or resistivity associated with the formation material. For example, the determination can be based on the known effects of particular properties of formation material with respect to the arcing and sparking that normally occurs when performing pulse power drilling operations on the same or similar formation materials.

Example Computer

FIG. 9 is a block diagram depicting an example computer system that may be utilized to implement operations for implementing a formation testing operation in accordance with some embodiments. The computer system includes a processor 901 (possibly including multiple processors, multiple cores, multiple nodes, and/or implementing multi-threading, etc.). The computer system includes a memory 907. The memory 907 may be system memory (e.g., one or more of cache, SRAM, DRAM, etc.) or any one or more of the above already described possible realizations of machine-readable media. The computer system also includes a bus 903 (e.g., PCI, ISA, PCI-Express, Infini-Band® bus, NuBus, etc.) and a network interface 905 which may comprise a Fiber Channel, Ethernet interface, SONET, or other interface.

The computer 900 also includes an analyzer 911 and a controller 915. Analyzer 911 is configured to perform the analysis the drilling fluids, formation fluids, cuttings (as described above). The controller 915 can control various downhole operations based on the analysis (as described above). Analyzer 911 may comprise hardware, software, firmware, or a combination thereof. Formation test system 911 may be configured similarly to data processing system 162 in FIG. 1.

Variations

While the aspects of the disclosure are described with reference to various implementations and exploitations, it will be understood that these aspects are illustrative and that the scope of the claims is not limited to them. In general, techniques for implementing formation testing as described herein may be performed with facilities consistent with any hardware system or systems. Plural instances may be provided for components, operations or structures described herein as a single instance. Finally, boundaries between various components, operations and data stores are somewhat arbitrary, and operations are illustrated in the context of specific illustrative configurations. Other allocations of functionality are envisioned and may fall within the scope of the disclosure. In general, structures and functionality presented as separate components in the example configurations may be implemented as a combined structure or component. Similarly, structures and functionality presented as a single component may be implemented as separate components.

The flowcharts are provided to aid in understanding the illustrations and are not to be used to limit scope of the claims. The flowcharts depict example operations that can vary within the scope of the claims. Additional operations may be performed; fewer operations may be performed; the operations may be performed in parallel; and the operations may be performed in a different order. It will be understood that each block of the flowchart illustrations and/or block diagrams, and combinations of blocks in the flowchart illustrations and/or block diagrams, can be implemented by program code. The program code may be provided to a processor of a general purpose computer, special purpose computer, or other programmable machine or apparatus.

As will be appreciated, aspects of the disclosure may be embodied as a system, method or program code/instructions stored in one or more machine-readable media. Accordingly, aspects may take the form of hardware, software (including firmware, resident software, micro-code, etc.), or a combination of software and hardware aspects that may all generally be referred to herein as a "circuit," "module" or "system." The machine-readable medium may be a machine readable signal medium or a machine readable storage medium. A machine readable storage medium may be, for example, but not limited to, a system, apparatus, or device, that employs any one of or combination of electronic, magnetic, optical, electromagnetic, infrared, or semiconductor technology to store program code. Use of the phrase "at least one of" preceding a list with the conjunction "and" should not be treated as an exclusive list and should not be construed as a list of categories with one item from each category, unless specifically stated otherwise.

EXAMPLE EMBODIMENTS

Embodiment 1: A method comprising determining a concentration of at least one chemical reaction product in a drilling fluid that has interacted with a plasma discharge proximate formation material; determining a relation between arc and spark of the plasma discharge based, at least in part, on the at least one chemical reaction product; and determining at least one of porosity and permeability of the formation material based, at least in part, on the relation between arc and spark. Said determining at least one of porosity and permeability of the formation material may comprise determining permeability of the formation material as a function, at least in part, of an increasing fraction of the plasma discharge that is arc. Said determining permeability of the formation material may comprise determining porosity of the formation material as a function, at least in part, of an increasing fraction of the plasma discharge that is spark. The method may further comprise determining a volume of hydrogen gas within effluent drilling fluid, and wherein determining the relation between arc and spark of the plasma discharge comprises determining the relation between arc and spark based, at least in part, on the determined volume of hydrogen gas. Said determining a relation between arc and spark of the plasma discharge may comprise correlating relative proportions of arc and spark of the plasma discharge to the concentration of the at least one chemical reaction product. Correlating relative proportions of arc and spark of the plasma discharge to the concentration of the at least one chemical reaction product may comprise determining a ratio of arc to spark based, at least in part, on the concentration of the at least one chemical reaction product. Said determining at least one of porosity and permeability of the formation material may include determining permeability of the formation material based, at least in part, on a determined porosity of the formation material. Determining porosity of the formation material may include determining porosity of cuttings within an effluent drilling fluid. Determining porosity of cuttings may comprise measuring a volume of gas obtained per unit formation material removed during drilling. Said determining at least one of porosity and permeability of the formation material may include determining porosity or permeability of the formation material based, at least in part, on material properties of the cuttings.

Embodiment 2: A non-transitory, computer-readable medium having instructions stored thereon that are executable by a computing device, the instructions to: determine a concentration of at least one chemical reaction product in a drilling fluid that has interacted with a plasma discharge proximate formation material; determine a relation between arc and spark of the plasma discharge based, at least in part, on the at least one chemical reaction product; and determine at least one of porosity and permeability of the formation material based, at least in part, on the relation between arc and spark. Said determining at least one of porosity and permeability of the formation material may comprise determining permeability of the formation material as a function, at least in part, of an increasing fraction of the plasma discharge that is arc. Said determining permeability of the formation material may comprise determining porosity of the formation material as a function, at least in part, of an increasing fraction of the plasma discharge that is spark. The non-transitory, computer-readable medium may further comprise instructions to determine a volume of hydrogen gas within effluent drilling fluid, and wherein determining the relation between arc and spark of the plasma discharge comprises determining the relation between arc and spark based, at least in part, on the determined volume of hydrogen gas. Said determining a relation between arc and spark of the plasma discharge may comprise correlating relative proportions of arc and spark of the plasma discharge to the concentration of the at least one chemical reaction product. Correlating relative proportions of arc and spark of the plasma discharge to the concentration of the at least one chemical reaction product may comprise determining a ratio of arc to spark based, at least in part, on the concentration of the at least one chemical reaction product. Said determining at least one of porosity and permeability of the formation material may include determining permeability of the formation material based, at least in part, on a determined porosity of the formation material. Determining porosity of the formation material may include determining porosity of cuttings within an effluent drilling fluid. Determining porosity of cuttings may comprise measuring a volume of gas obtained per unit formation material removed during drilling. Said determining at least one of porosity and permeability of the formation material may include determining porosity or permeability of the formation material based, at least in part, on material properties of the cuttings.

The invention claimed is:

1. A method comprising:
    performing pulse power drilling using an electrical discharge generated by a pulse power drilling apparatus operating in a downhole environment;
    determining a concentration of at least one chemical reaction product in a drilling fluid that has interacted with a plasma discharge proximate a formation material;
    determining a relation between arc and spark of the plasma discharge based, at least in part, on the at least one chemical reaction product;
    determining at least one of porosity and permeability of the formation material based, at least in part, on the relation between arc and spark.

2. The method of claim 1, wherein said determining at least one of porosity and permeability of the formation material comprises determining permeability of the formation material as a function, at least in part, of an increasing fraction of the plasma discharge that is arc.

3. The method of claim 1, wherein said determining permeability of the formation material comprises determining porosity of the formation material as a function, at least in part, of an increasing fraction of the plasma discharge that is spark.

4. The method of claim 1, further comprising determining a volume of hydrogen gas within effluent drilling fluid, and wherein determining the relation between arc and spark of the plasma discharge comprises determining the relation between arc and spark based, at least in part, on the determined volume of hydrogen gas.

5. The method of claim 1, wherein said determining at least one of porosity and permeability of the formation material includes determining porosity or permeability of the formation material based, at least in part, on material properties of the cuttings.

6. The method of claim 1, wherein said determining a relation between arc and spark of the plasma discharge comprises correlating relative proportions of arc and spark of the plasma discharge to the concentration of the at least one chemical reaction product.

7. The method of claim 6, wherein correlating relative proportions of arc and spark of the plasma discharge to the concentration of the at least one chemical reaction product comprises determining a ratio of arc to spark based, at least in part, on the concentration of the at least one chemical reaction product.

8. The method of claim 1, wherein said determining at least one of porosity and permeability of the formation material includes determining permeability of the formation material based, at least in part, on a determined porosity of the formation material.

9. The method of claim 8, wherein determining porosity of the formation material includes determining porosity of cuttings within an effluent drilling fluid.

10. The method of claim 9, wherein determining porosity of cuttings comprises measuring a volume of gas obtained per unit formation material removed during drilling.

11. A non-transitory, computer-readable medium having instructions stored thereon that are executable by a computing device, the instructions to:
- determine a concentration of at least one chemical reaction product in a drilling fluid that has interacted with a plasma discharge proximate formation material;
- determine a relation between arc and spark of the plasma discharge based, at least in part, on the at least one chemical reaction product; and
- determine at least one of porosity and permeability of the formation material based, at least in part, on the relation between arc and spark.

12. The non-transitory, computer-readable medium of claim 11, wherein said determining at least one of porosity and permeability of the formation material comprises determining permeability of the formation material as a function, at least in part, of an increasing fraction of the plasma discharge that is arc.

13. The non-transitory, computer-readable medium of claim 11, wherein said determining permeability of the formation material comprises determining porosity of the formation material as a function, at least in part, of an increasing fraction of the plasma discharge that is spark.

14. The non-transitory, computer-readable medium of claim 11, further comprising instructions to determine a volume of hydrogen gas within effluent drilling fluid, and wherein determining the relation between arc and spark of the plasma discharge comprises determining the relation between arc and spark based, at least in part, on the determined volume of hydrogen gas.

15. The non-transitory, computer-readable medium of claim 11, wherein said determining at least one of porosity and permeability of the formation material includes determining porosity or permeability of the formation material based, at least in part, on material properties of the cuttings.

16. The non-transitory, computer-readable medium of claim 11, wherein said determining a relation between arc and spark of the plasma discharge comprises correlating relative proportions of arc and spark of the plasma discharge to the concentration of the at least one chemical reaction product.

17. The non-transitory, computer-readable medium of claim 16, wherein correlating relative proportions of arc and spark of the plasma discharge to the concentration of the at least one chemical reaction product comprises determining a ratio of arc to spark based, at least in part, on the concentration of the at least one chemical reaction product.

18. The non-transitory, computer-readable medium of claim 11, wherein said determining at least one of porosity and permeability of the formation material includes determining permeability of the formation material based, at least in part, on a determined porosity of the formation material.

19. The non-transitory, computer-readable medium of claim 18, wherein determining porosity of the formation material includes determining porosity of cuttings within an effluent drilling fluid.

20. The non-transitory, computer-readable medium of claim 19, wherein determining porosity of cuttings comprises measuring a volume of gas obtained per unit formation material removed during drilling.

* * * * *